(12) United States Patent
Sato et al.

(10) Patent No.: US 6,687,521 B2
(45) Date of Patent: Feb. 3, 2004

(54) NONINVASION BIOLOGICAL OPTICAL MEASURING INSTRUMENT, MEASURED PORTION HOLDING DEVICE, AND METHOD FOR MANUFACTURING THE SAME

(75) Inventors: Katsuhiko Sato, Hamamatsu (JP);
Nobuhiro Morita, Hamamatsu (JP);
Yukio Ueda, Hamamatsu (JP);
Toshihiko Mizuno, Hamamatsu (JP);
Shigeru Sakamoto, Hamamatsu (JP);
Koji Yamanaka, Hamamatsu (JP);
Toshiyuki Tanaka, Hamamatsu (JP);
Hideo Takahashi, Hamamatsu (JP);
Keiji Suyama, Hamamatsu (JP);
Seiichiro Hashimoto, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 0 days.

(21) Appl. No.: 10/182,818

(22) PCT Filed: Feb. 5, 2001

(86) PCT No.: PCT/JP01/00793

§ 371 (c)(1),
(2), (4) Date: Aug. 2, 2002

(87) PCT Pub. No.: WO01/56472

PCT Pub. Date: Aug. 9, 2001

(65) Prior Publication Data

US 2003/0023171 A1 Jan. 30, 2003

(30) Foreign Application Priority Data

Feb. 3, 2000 (JP) ..................................... P2000-026322
Feb. 10, 2000 (JP) ..................................... P2000-033714
Dec. 14, 2000 (JP) ..................................... P2000-380484

(51) Int. Cl.$^7$ ................................................ A61B 5/00
(52) U.S. Cl. ....................................... 600/344; 600/310
(58) Field of Search ................................ 600/310, 322, 600/323, 344, 473, 476; 264/222, 227

(56) References Cited

U.S. PATENT DOCUMENTS

| 4,617,429 A | * 10/1986 | Bellafiore ..................... 381/324 |
| 4,663,102 A | * 5/1987 | Brenman et al. ............ 264/222 |
| 5,237,178 A | 8/1993 | Rosenthal et al. ........... 250/341 |
| 6,006,120 A | * 12/1999 | Levin ......................... 600/323 |

FOREIGN PATENT DOCUMENTS

| JP | 60-236631 | 11/1985 |
| JP | 6-30916 | 2/1994 |
| JP | 6-503728 | 4/1994 |
| JP | 6-245925 | 9/1994 |
| JP | 7-506497 | 7/1995 |
| JP | 8-207942 | 8/1996 |
| JP | 9-509739 | 9/1997 |
| JP | 9-512446 | 12/1997 |
| JP | 10-33512 | 2/1998 |

* cited by examiner

*Primary Examiner*—Eric F. Winakur
(74) *Attorney, Agent, or Firm*—Morgan, Lewis & Bockius LLP

(57) ABSTRACT

The present device is equipped with a measurement site holder 3 that is constructed using a negative impression of the measurement site 10. As a result, variation in the measured values caused by the non-uniform distribution of components in the measurement site 10 is reduced, so that variation in the measured values caused by variations in the light path length accompanying variations in the shape of the measurement site 10, and by variations in blood flow or the like that accompany differences in the contact pressure, can be reduced. Since living-body information and measurement parameters for the patient are recorded on a recording medium 11 mounted on a measurement site holder 3 for the exclusive use of the individual patient, the erroneous acquisition of living-body information for individual patients can be prevented, and reproducible measurements can be performed.

25 Claims, 26 Drawing Sheets

Fig.8

| | FOURIER TRANSFORM SPECTROSCOPIC DEVICE | PHOTO-DETECTOR | MEASUREMENT WAVELENGTH RANGE (μm) | RANGE OF MEASURED BLOOD SUGAR LEVELS (mg/dl) | CORRELATION COEFFICIENT BETWEEN MEASURED AND PREDICTED BLOOD SUGAR LEVELS | ROOT MEAN SQUARE ERROR OF PREDICTION (mg/dl) |
|---|---|---|---|---|---|---|
| FIRST EMBODIMENT | SPECTRUM 2000 FTIR MANUFACTURED BY PERKIN-ELMER CO. (MICHELSON INTERFEROMETER) | InGaAs-PIN PHOTO-DIODE G5832-05 MANUFACTURED BY HAMAMATSU PHOTONICS K.K. | 1.0~1.38 | 114~244 | 0.85 | 23 |
| FOURTH EMBODIMENT | MULTI-CHANNEL FOURIER TRANSFORM SPECTROSCOPIC DEVICE (SAVART PLATE - BIREFRINGENT INTERFEROMETER) | InGaAs LINEAR IMAGE SENSOR G7231-256 MANUFACTURED BY HAMAMATSU PHOTONICS K.K. | 0.95~1.345 | 109~225 | 0.94 | 15 |

NONINVASION BIOLOGICAL OPTICAL MEASURING INSTRUMENT, MEASURED PORTION HOLDING DEVICE, AND METHOD FOR MANUFACTURING THE SAME

TECHNICAL FIELD

The present invention relates to an optical bioinstrumentation device for noninvasively measuring the concentrations of components in the living body by means of light, a measurement site holder in which the measurement site is placed, and a method of manufacturing the same.

BACKGROUND ART

For example, devices which perform spectroscopic measurements and devices which perform magnetic measurements are known as devices for acquiring information concerning the living body of a patient being examined in a noninvasive manner (noninvasive meaning that there is no need to insert a device or instrument through the skin or bodily orifices for the purpose of diagnosis or treatment). The devices described in Japanese Patent Application Laid-Open No. S60-236631 and U.S. Pat. No. 5,237,178 perform quantitative measurements of components in the living body in noninvasive manner by spectroscopic means.

The devices described in these patents are devices that measure the glucose concentration (blood sugar level) in the living body of the patient being examined in a noninvasive manner. In the device described in Japanese Patent Application Laid-Open No. S60-236631, a construction in which the ear lobe (measurement site) of the patient being examined is illuminated from the outside with light, and the transmitted light that passes through the ear lobe is detected by a photo-detector attached to the inside of the ear lobe by means of adhesive tape, a strap or the like, and a construction in which a photo-detector is applied to the surface of the patient's body (measurement site), and scattered and reflected light are detected, are disclosed.

In the device described in U.S. Pat. No. 5,237,178, a construction is disclosed in which a finger tip stopper and a sponge rubber used to hold the finger are used as finger insertion means for positioning the finger, and the transmitted light that is transmitted through the finger (measurement site) is detected by a photo-detector.

Furthermore, in conventional noninvasive measuring devices, living-body information for a plurality of patients is acquired separately, and the living-body information thus acquired for individual patients is recorded on a recording medium which is installed inside or outside the abovementioned measuring device. The living-body information for individual patients that is recorded on this recording medium is read out on subsequent occasions when living-body information is to be acquired by these patients, and (for example) when diagnoses are made by physicians or when judgements are made by the patients themselves.

DISCLOSURE OF THE INVENTION

However, in the case of such prior art, the measurement conditions fluctuate according to the positional relationship between the measurement site and the photo-detector, so that the problem of measurement error arises.

Specifically, since the distribution of components in the living body is not uniform, the light path at the measurement site shifts (for example) if there is any shift in the mounting position of the photo-detector with respect to the measurement site, or any shift in the set position of the measurement site with respect to the device in which the photo-detector is mounted, so that the information contained in the light that is emitted from the living body fluctuates, thus resulting in the occurrence of measurement error. Furthermore, in cases where measurements are performed with the photo-detector pressed against the measurement site, there is a variation in the manner of flow of subcutaneous blood as a result of fine differences in the pressing force, in addition to a variation in the light path length accompanying shape deformation of the measurement site; as a result, the variation in measurements is increased, so that measurement error occurs.

Furthermore, since living-body information for numerous patients is recorded on the recording medium installed in a conventional measuring device, living-body information for individual patients may be erroneously acquired. In cases where living-body information for individual patients is thus erroneously acquired, this may lead to (for example) erroneous diagnoses by physicians or erroneous judgements by the patients themselves.

When living-body information is acquired by patients on subsequent occasions, and (for example) when diagnoses are made by physicians or when judgements are made by the patients themselves, the living-body information that is recorded on the recording medium installed in the measuring device must be read out. Accordingly, the same measuring device must be used, so that the convenience to the patients is poor.

It would appear that these problems are becoming more conspicuous as a result of the increasing commonness of living-body measurements for multiple numbers of patients in the household with the development of an increasingly aging society in recent years.

The present invention was devised in order to solve such problems. It is an object of the present invention to provide a noninvasive optical bioinstrumentation device which allows highly precise quantitative measurements of components in the living body. Furthermore, it is also an object of the present invention to provide a measurement site holder used in such an apparatus, which prevents erroneous diagnoses and erroneous judgements, and which offers increased convenience to the user.

The noninvasive living body optical measuring device of the present invention is a noninvasive optical bioinstrumentation device in which a specified measurement site in the living body is illuminated with light, the light that is transmitted through this measurement site or the light that is scattered and reflected by this measurement site is detected by a photo-detection system, and the concentrations of components in the living body are measured from this detected light, this device being wherein the device is equipped with a measurement site holder which is constructed using a negative impression of the measurement site, and in which the measurement site is placed at the time of light detection.

In a noninvasive optical bioinstrumentation device constructed as described above, the measurement site holder is constructed using a negative impression of the measurement site; accordingly, this measurement site holder can be caused to fit or conform to the shape of the patient's measurement site. Accordingly, the measurement site can be positioned with good precision when the measurement site is placed in the measurement site holder at the time of light detection, so that shifts in the light path at the measurement site are reduced compared to those in a conventional device.

Consequently, variations in the measured values caused by the non-uniform distribution of components in the living body are reduced, and variations in the shape of the measurement site are reduced compared to those seen in conventional devices, so that variations in the measured values caused by variations in the light path length accompanying changes in the shape of the measurement site, or by variations in blood flow due to differences in the contact pressure or the like, can be reduced.

Here, if the measurement site holder has a detachable structure, then the same device can be used in common by numerous patients, by selecting a measurement site holder that fits or conforms to the shape of the patient's measurement site, and mounting this measurement site holder on the device.

Furthermore, if the measurement site holder is manufactured as a negative impression of the measurement site for each individual patient, then this measurement site holder will conform to the shape of the measurement site, so that variation in the measured values can be minimized.

Furthermore, if the measurement site holder is equipped with an opening part that allows the illumination of the measurement site with light, and an opening part that makes it possible to guide the transmitted light or scattered and reflected light from the measurement site into the photo-detection system, or if the measurement site holder is equipped with a single opening part that allows the illumination of the measurement site with light and that makes it possible to guide the scattered and reflected light from the measurement site into the photo-detection system, then the position at which light is incident on the measurement site and the position at which light is emitted from the measurement site can be accurately fixed, so that variation in the measured values is further greatly reduced.

Furthermore, if the inside contact surface of the measurement site holder that contacts the measurement site is coated with a coating material that absorbs light in the measurement wavelength region, then fine variations in the light path length in the living body caused by the reflection of light at the contact surface between the measurement site holder and the measurement site can be prevented, so that variation in the measured values is further greatly reduced.

Furthermore, it is desirable that the photo-detection system be equipped with a birefringent interferometer which converts the transmitted light or scattered and reflected light into split light by using a polarized light splitting birefringent element to split the light into polarized light with mutually perpendicular vibrational planes, and which causes this split light to converge so that an interferogram that makes it possible to measure the concentrations of components in the living body is obtained.

As a result, since an interferogram based on the light that is transmitted through the measurement site of the living body or the light that is scattered and reflected by this measurement site is obtained via a polarized light splitting birefringent element, the concentrations of components in the living body can be measured. Such a birefringent interferometer equipped with a polarized light splitting birefringent element has a simple construction without any mechanical driving parts; accordingly, such an interferometer can be made compact and light-weight, and the resistance to vibration is also improved.

Furthermore, it is desirable that the birefringent interferometer be equipped with a polarizer which polarizes the transmitted light or scattered and reflected light and directs this light onto the polarized light splitting birefringent element, an analyzer which polarizes the split light emitted from the polarized light splitting birefringent element, converging means which cause convergence of the light polarized by the analyzer and thus form an interferogram, and a photo-detector which detects this interferogram.

As a result, background components can be removed and the intensity of the interferogram can be doubled by taking the difference between an interferogram obtained with the directions of polarization of the polarizer and analyzer set parallel to each other and an interferogram obtained with the directions of polarization of the polarizer and analyzer set perpendicular to each other; accordingly, the S/N ratio can be increased even further.

Furthermore, if light adjustment means that narrow down or reduce the transmitted light or scattered and reflected light are installed between the measurement site holder and the birefringent interferometer, the light that is incident on the birefringent interferometer can be adjusted by being narrowed down or reduced; accordingly, the S/N ratio of the detected light can be increased even further.

Furthermore, the polarized light splitting birefringent element may be either a Savart plate or a Wollaston prism. As a result, the polarized light splitting birefringent element can easily be constructed, and a noninvasive optical bioinstrumentation device can be appropriately realized.

This measurement site holder is a measurement site holder for the exclusive use of each individual patient which is mounted on the side of the measuring device in order to acquire living-body information from the patient, and in which the measurement site of this patient is placed. This measurement site holder is wherein the holder is equipped with a recording medium which records living-body information acquired from the individual patient and/or measurement parameters used at the time of measurement, and is constructed so that the holder is detachable with respect to the measuring device side.

In the case of a measurement site holder constructed as described above, the measurement site of the patient is placed in a measurement site holder for the exclusive use of the individual patient which is mounted on the side of the measuring device, so that living-body information that is acquired for this patient is recorded on the recording medium of the measurement site holder that is currently mounted on the side of the measuring device.

Since this measurement site holder is made detachable with respect to the side of the measuring device, the measurement site holder can be carried/stored by the patient himself, and there is a one-to-one relationship between the measurement site holder for the individual patient that is thus carried/stored and used at the time of measurement, and the living-body information for this individual patient. Accordingly, the erroneous reading of living-body information for individual patients is prevented; furthermore, as a result of the use of a measurement site holder for the individual patient equipped with such a recording medium, the acquisition of living-body information for this patient on subsequent occasions, and the read-out of living-body information recorded for this patient, can be accomplished using a device other than the measuring device used to perform measurements.

Here, working curves for the individual patient and information regarding living-body components of the individual patient determined using such working curves may be cited as concrete examples of living-body information for the individual patient that is recorded on the recording medium. Various types of information may be cited as examples of such information regarding living-body components; blood sugar levels may be cited as a concrete example.

Furthermore, in concrete terms, a construction in which the measurement site in the measurement site holder is illuminated with light, the light that is transmitted through this measurement site or the light that is scattered and reflected by this measurement site is detected, and living-body information for the patient is acquired in a noninvasive manner on the basis of this detected light, may be cited as an example of the construction used to acquire living-body information for the patient.

Here, if a measurement site holder for the exclusive use of the individual patient is manufactured so that this holder conforms to the shape of the measurement site of the individual patient, the measurement site holder and measurement site show rough agreement; accordingly, the patient is much more effectively prevented from accidentally taking the wrong measurement site holder.

The abovementioned measurement site holder is a measurement site holder which is attached to a base that is disposed in the light path of the light that is incident on the photo-detection system. This measurement site holder is equipped with a main body part which has an opening into which the measurement site is inserted, and a base plate to which at least the tip end portion of the main body part is fastened, and which can be detachably mounted on a base. Furthermore, in cases where a portion of the measurement site protrudes from the measurement site holder, or in cases where there is no need to hold this protruding portion, it is desirable that an opening part be provided. It is desirable that the outside surface of this measurement site holder be coated with a coating in order to block external light, and that the inside of the measurement site holder be coated with a black coating material in order to prevent light that has passed through the tissues from escaping to the outside and re-entering the tissues, or that an optical filter be provided which is attached to the outside surface of the main body part.

An appropriate method for manufacturing the measurement site holder comprises the steps of forming a first resin mold which has an inside surface that matches the shape of the outside surface of the measurement site, forming a second resin mold which has an outside surface of the same shape as the outside surface of the abovementioned measurement site by introducing a resin into the first resin mold, transporting the abovementioned second resin mold to a specified factory, and forming a measurement site holder which has an inside surface that matches the shape of the outside surface of the abovementioned second resin mold at the abovementioned factory.

BRIEF DESCRIPTION OF THE DRAWINGS

FIG. 8 is a table which shows the measurement results for blood levels obtained by means of the noninvasive optical bioinstrumentation devices of the first embodiment and fourth embodiment;

BEST MODE FOR CARRYING OUT THE INVENTION

Figure 1:
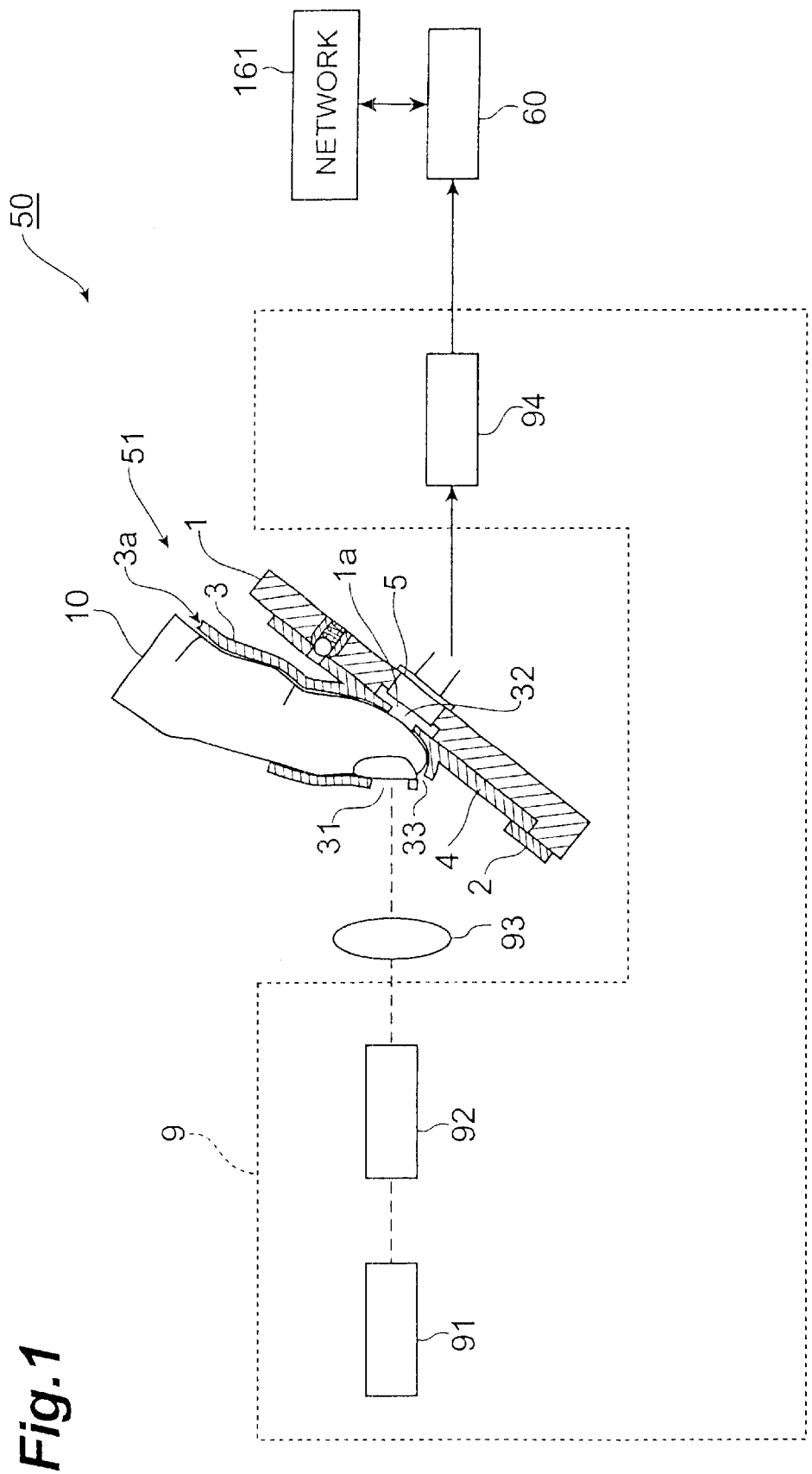
FIG. 1 is a schematic structural diagram which shows a noninvasive optical bioinstrumentation device constituting a first embodiment of the present invention.
Figure 2A:
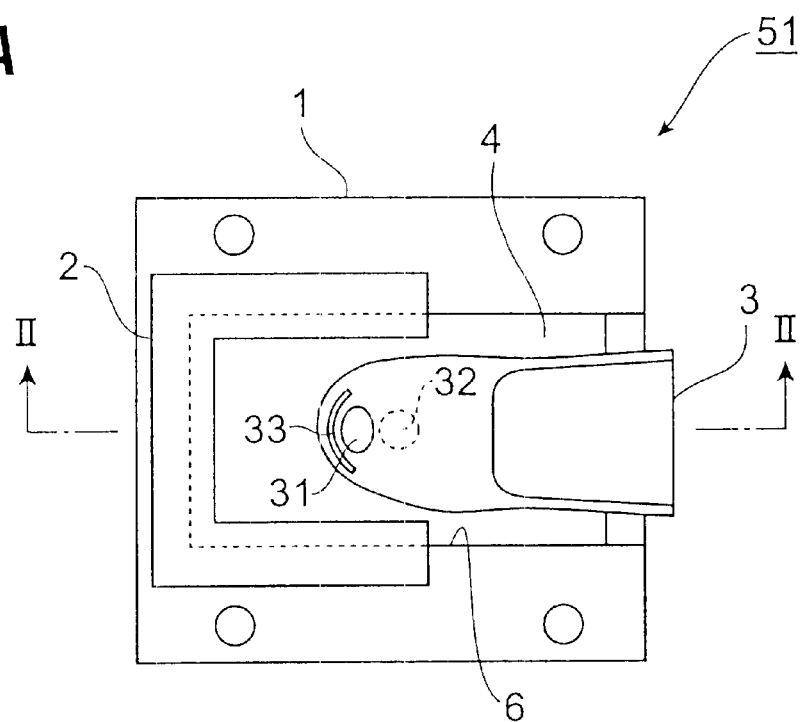
FIG. 2A is a plan view of a measurement site holding device equipped with the measurement site holder shown in FIG. 1.

Embodiments of the present invention will be described below with reference to the attached figures.
First Embodiment FIG. 1 is a schematic structural diagram which shows a noninvasive optical bioinstrumentation device constituting a first embodiment of the present invention. FIG. 2A is a plan view of a measurement site holding device equipped with the measurement site holder shown in FIG. 1, and FIG. 2B is a sectional view along line II—II of the device shown in FIG. 2A.

In the noninvasive optical bioinstrumentation device 50 of the present embodiment, as is shown in FIG. 1, the living-body measurement site is a finger (finger tip) 10. This noninvasive optical bioinstrumentation device 50 comprises a measurement site holder 3 which has a main body part 3a in which the finger 10 is placed, a measurement site holding device 51 in which this measurement site holder 3 is mounted, and which is equipped with a photo-detector (photo-detection system) 5 that detects the light that is transmitted through the finger 10 placed in the main body part 3a of the abovementioned measurement site holder 3, a Fourier transform near infrared spectroscopic analyzer 9 in which light from a light source 91 is emitted to the outside via a Michaelson interferometer 92 so that the finger 10 placed inside the main body part 3a of the measurement site holder 3 is illuminated, and a near infrared spectrum is obtained by subjecting a near infrared interferogram detected by the photo-detector 5 on the basis of the light transmitted through the finger 10 to a Fourier transform using a computer system part 94, and a computer 60 which prepares a working curve on the basis of this near infrared spectrum, and predicts blood sugar levels on the basis of this working curve.

Figure 2B:
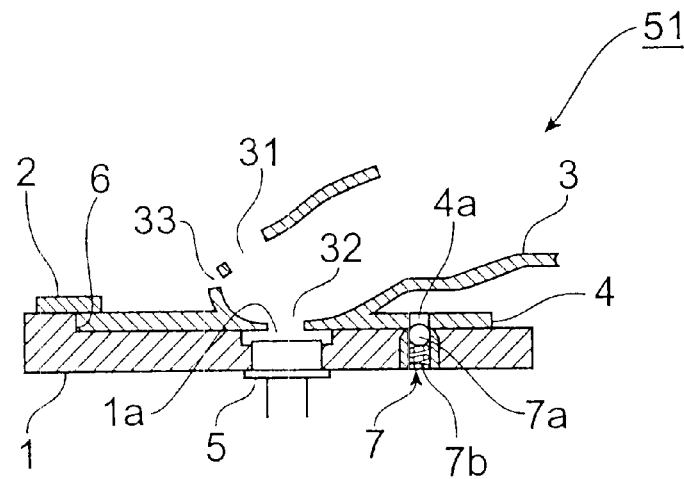
FIG. 2B is a sectional view along line II—II of the device shown in FIG. 2A.

As is shown in FIGS. 2A and 2B, the measurement site holding device 51 is equipped with a base 1 which has a rectangular shape and which is attached to the main body side of the noninvasive optical bioinstrumentation device 50. As is shown in FIG. 2B, an opening part 1a which passes vertically through the base 1 is formed in the approximate center of this base 1, and a photo-detector 5 is mounted inside this opening part 1a. This photo-detector 5 is disposed so that the photo-detection part is visible from the upper side of the opening part 1a.

As is shown in FIG. 2B, a rectangular base plate 4 which holds the abovementioned measurement site holder 3 on the upper part of this base plate 4 is detachably mounted on the upper surface of the base 1. The base 1 is disposed in the light path along which light is incident on the photo-detection system 5 from the light illuminating system 91, 92, 93, and if the measurement site holder 3 is installed on the base 1, then the finger (measurement site) 10 placed inside the measurement site holder 3 will be positioned in the abovementioned light path.

The base 1 has a rectangular groove 6 (in the upper surface of the base 1) which is formed so that the base plate 4 can be inserted from the horizontal direction, a U-shaped or C-shaped base plate supporting part 2 which surrounds the upper part of the closed side (the left side in FIG. 2B) of the groove 6 on three sides, an opening part 7 which passes vertically through the base 1 in a specified position located further toward the open side of the abovementioned groove 6 than an opening part 1a formed in the groove 6, a spherical stopper 7a which is disposed inside this opening part 7, and a spring 7b which drives this stopper 7a upward. This base 1 is constructed in such a manner that when the base plate 4 is inserted along the groove 4 from the open side of the groove 6 so that the base plate 4 is caused to abut the close-side end portion of the groove 6, the spherical stopper 7a is engaged in an opening part 4a formed in the base plate 4, so that the base plate 4 is positioned on the base 1, and is always fixed in the same position; furthermore, the base plate 4, i.e., the measurement site holder 3, is detachably mounted on the upper surface of the base 1.

The main body part 3a of the measurement site holder 3 mounted on the upper part of this base plate 4 constitutes the characterizing feature of the present embodiment. This main body part 3a is manufactured as a negative impression of the finger of each individual patient (the method of manufacture will be described later). As is shown in FIG. 1, an opening part 31 used for the incidence of light is formed in a position that corresponds to a specified position (the nail surface in the present embodiment) on the finger 10 that is placed on the main body pat 3a of the measurement site holder 3, and an opening part 32 used for light detection (light emission) is formed in a position corresponding to the opposite surface of the finger 10 from the nail surface; furthermore, a nail opening part 33 is formed in position corresponding to the direction of extension of the nail of the finger 10.

The opening part 31 used for illumination with light is an opening part which is positioned on the light path from the Michaelson interferometer 92 of the Fourier transform near infrared spectroscopic analyzer 9 when the base plate 4 on which the measurement site holder 3 is installed is mounted on the base 1, and the finger 10 is placed inside the main body part (main body part of the measurement site holder) 3a of the measurement site holder 3; this opening part 31 conducts light that is focused by a focusing lens 93 positioned between the Michaelson interferometer 92 and the light-illumination opening part 31 into the interior of the main body part 3a of the measurement site holder 3, and makes it possible to illuminate a specified position on the finger 10. The light-detection opening part 32 is an opening part which is positioned coaxially with the opening part 1a in which the photo-detection part of the photo-detector 5 is visible, and which makes it possible to guide the transmitted light that passes through the finger 10 to the photo-detector 5.

Next, the method used to manufacture the measurement site holder 3 (main body part 3a) in which the abovementioned light-illumination opening part 31, light-detection opening part 32 and nail opening part 33 are formed in a negative impression will be described. First, a material which has sufficient fluidity to allow application as a coating to the surface of the finger 10, or which softens at a relatively low temperature and requires little stress to be deformed when softened, and which furthermore hardens in a short time and has sufficient strength with a high dimensional stability during hardening, and is optically stable over a long period of time, is prepared as the molding material for the negative impression. In concrete terms, for example, impression materials or resins that polymerize at ordinary temperatures, which are used in dental treatments, and thermoplastic resins or the like which are used in plastic surgery and radiation therapy, are desirable. Here, a resin that polymerizes at ordinary temperatures will be used in the present embodiment.

Furthermore, in a state in which the surface of the finger 10 is thinly coated with a peeling agent such as vaseline or the like, and (for example) the finger 10 is held in the air so that there is no deformation in the shape of the finger 10, the surface of the finger 10 is brush-coated with an ordinary-temperature polymerizing resin using a brush coating method. Here, for example, brush coating is performed as far as the vicinity of the second joint from the finger tip (proximal interphalangeal joint). In this case, in order to alleviate the burden on the patient, it is desirable to us GC Unifast Trad (manufactured by GC Corp.) or the like, which has a short hardening time of 3 minutes. Furthermore, following the completion of brush coating, the finger 10 is allowed to stand "as is" in a fixed state for approximately 3 minutes. Afterward, the finger 10 is removed, and the ordinary-temperature polymerizing resin is sufficiently hardened so that a negative impression of the finger 10 is obtained. As was described above, such a negative impression is prepared for each individual patient. Accordingly, the respective negative impressions match the finger shapes of the individual patients.

Once a negative impression has thus been obtained, the abovementioned light-illumination opening part 31 and light-detection opening part 32 are opened in the negative impression. Here, since the nail of the finger grows as time passes, the elongated nail is a factor that alters the placement position of the finger 10 with respect to the negative impression (i.e., a factor that lowers the positioning precision of the finger 10 with respect to the negative impression). Accordingly, the abovementioned nail opening part 33 is opened in the negative impression along with the light-illumination opening part 31 and light-detection opening part 32. Furthermore, the inside contact surface of the negative impression that contacts the finger 10 is coated with (for example) a delustering black coating material or the like as a coating material that absorbs light of the measurement wavelength, thus producing the measurement site holder 3 shown in FIGS. 1, 2A and 2B.

Next, the operation of a noninvasive optical bioinstrumentation device 50 equipped with a measurement site holder 3 constructed as described above will be described. First, the base plate 4 holding the measurement site holder (individual patient measurement site holder) 3 manufactured for the patient that is the object of measurement is mounted on the base 1. In this case, the measurement site holder 3 on the base plate 4 is positioned and mounted on the base 1 with high precision by means of the abovementioned groove 6, base plate supporting part 2, stopper 7a and the like.

Next, the patient inserts the finger 10 used in the preparation of the negative impression into the measurement site holder 3. In this case, since the measurement site holder 3 was manufactured as a negative impression of the finger for each individual patient, the measurement site holder 3 matches the finger shape of the individual patient. Accordingly, the finger 10 is positioned with high precision, and the finger 10 uniformly contacts this measurement site holder 3. In this case, furthermore, even if the nail grows, this nail protrudes from the nail opening part 33, so that there is no interference with the high-precision positioning of the finger 10.

Next, in the measurement operation, light from the light source 91 is caused to enter the measurement site holder 3 via the Michaelson interferometer 92, focusing lens 93 and light-illumination opening part 31, so that a specified position on the finger 10 is illuminated. In this case, as was described above, the finger 10 is positioned with a high degree of precision, and contacts the measurement site holder 3 in a uniform manner. In addition, the measurement site holder 3 is positioned with a high degree of precision relative to the base 1. Accordingly, the incident light always illuminates substantially the same position on the finger 10, which shows no great variation in shape, so that the light that is transmitted through this finger 10 always passes through substantially the same position, and is received by the photo-detector 5 via the light-detection opening part 32.

The signal produced by a photo-electric conversion from this photo-detector 5 is input into the computer system part 94 so that a near infrared spectrum is obtained. This near infrared spectral information and blood sugar levels obtained by blood collection performed at the same time as the measurement of the near infrared spectrum are input into the computer 60, and a working curve for blood sugar levels is prepared on the basis of these respective types of information. This computer 60 stores this working curve as a data table in internal or external memory means, and reads out this working curve at the time of measurement of blood sugar levels, so that blood sugar levels are obtained by comparing the measured near infrared spectrum with this working curve.

Furthermore, in cases where the blood sugar levels of another patient are to be measured using this noninvasive optical bioinstrumentation device 50, the base plate 4 holding the abovementioned measurement site holder 3 is removed, and a base plate 4 holding a different measurement site holder 3 that has been manufactured for this other patient (and that matches the finger shape of this other patient) is mounted on the base 1, and measurements are performed. Furthermore, the working curves prepared by the computer 60 are prepared and stored in memory for each individual patient.

Thus, in the present embodiment, since the measurement site holder 3 is constructed using a negative impression of the finger for each individual patient, the measurement site holder 3 matches the shape of the finger of each patient. Accordingly, when the finger 10 is placed in the measurement site holder 3 at the time of light detection, the finger 10 is positioned with a high degree of precision, so that shifting of the light path in the finger 10 can be more or less prevented. Consequently, variation in the measured values caused by the non-uniform distribution of components in the living body can be minimized; furthermore, extremely fine variations in the shape of the finger 10 can be more or less prevented, so that variation in the measured values caused by variations in the light path length that accompany variations in the shape of the finger 10, and variations in blood flow that accompany fine differences in the contact pressure, can be minimized. Accordingly, blood sugar levels can be quantitatively measured with a high degree of precision.

Furthermore, since the measurement site holder 3 has a detachable structure, the same noninvasive optical bioinstrumentation device 50 can be shared by numerous patients by mounting measurement site holders 3 that were prepared for the individual patients and that match the fingers of the individual patients on this device 50. Accordingly, the blood sugar levels of numerous patients can be quantitatively measured using the same device 50.

Furthermore, since the measurement site holder 3 is equipped with a light-illumination opening part 31 that makes it possible to illuminate the finger 10 with light, and a light-detection opening part 32 that makes it possible to guide transmitted light from the finger 10 to a photo-detector 5, the position at which light is incident on the finger 10 and the position at which light is emitted from the finger 10 can be accurately determined, so that variation in the measured values can be greatly reduced. Accordingly, blood sugar levels can be measured with much higher precision.

Furthermore, since the inside of the measurement site holder 3 is coated with a coating material that absorbs light of the measurement wavelength, minute variations in the length of the light path inside the living body caused by the reflection of light at the contact interface between the measurement site holder 3 and finger 10 can be prevented, so that variation in the measured values can be greatly reduced. As a result, blood sugar levels can be measured with much higher precision. Furthermore, the measurement site holder 3 may also be equipped with a main body part 3a which consists of a resin containing a pigment or dye that absorbs light of the measurement wavelength, and which contacts the finger (measurement site) 10.

Here, in order to confirm the abovementioned effects of the measurement site holder 3, the present inventors performed the experiment described below using a system in which the abovementioned measurement site holder 3 was employed in the noninvasive optical bioinstrumentation device 50 (the noninvasive optical bioinstrumentation device 50 of the present embodiment shown in FIG. 1), and a system in which a universally known finger holder was employed instead of this measurement site holder 3. In this way, the inventors evaluated the precision of both systems (the measurement site holder 3 and finger holder).

The acceleration pulse wave sensor AS-120 of the Precaregraph AGP-200 manufactured by Misawa Home Institute of Research Development Co. Ltd. was used as a finger holder. A finger holder prepared by removing the light-emitting element and photo-detector of this finger holder, and respectively forming a light-illumination opening part and light-detection opening part in these positions, was fastened to the base plate 4 instead of the measurement site holder 3.

Furthermore, in this experiment, a Spectrum 2000 FTIR manufactured by Perkin-Elmer Inc. was used as the Fourier transform near infrared spectroscopic analyzer 9, and an InGaAs-PIN photodiode (G5832-05 manufactured by Hamamatsu Photonics K.K.) was used as the photo-detector 5. The measurement wavelength range was set at 1.0 to 1.38 μm.

Then, after fasting for approximately 12 hours, each patient was caused to ingest a saccharine liquid (Trelan G75 manufactured by Shimizu Pharmaceutical Co. Ltd., glucose content 75 g). Blood was collected by pricking a finger tip on the left hand before ingestion of the saccharine liquid, and every 10 minutes up to 2 hours following the ingestion of the saccharine liquid, and blood sugar levels were measured (analysis values according to a conventional method) using a compact electrode type blood sugar measuring device (Antosense II manufactured by Bayer-Sankyo(Bayer Medical Ltd.)). Meanwhile, measurements of the near infrared spectrum by means of the measurement site holder 3 and finger holder were performed using the right hand at the time that blood was collected from the abovementioned finger tip of the left hand. The days on which measurements were performed using the measurement site holder 3 and the days on which measurements were performed using the finger holder were different days.

The preparation of working curves was accomplished using a partial least squares (PLS) regression analysis, with the blood sugar level obtained by means of the abovementioned blood collection used as the objective variable, and the near infrared spectrum measured at the same time as blood collection used as the descriptive variable. The predicted values of blood sugar levels according to the near infrared spectrum were calculated using the working curves thus prepared. The cross validation method was used in order to evaluate the precision of the working curves.

Figure 3:
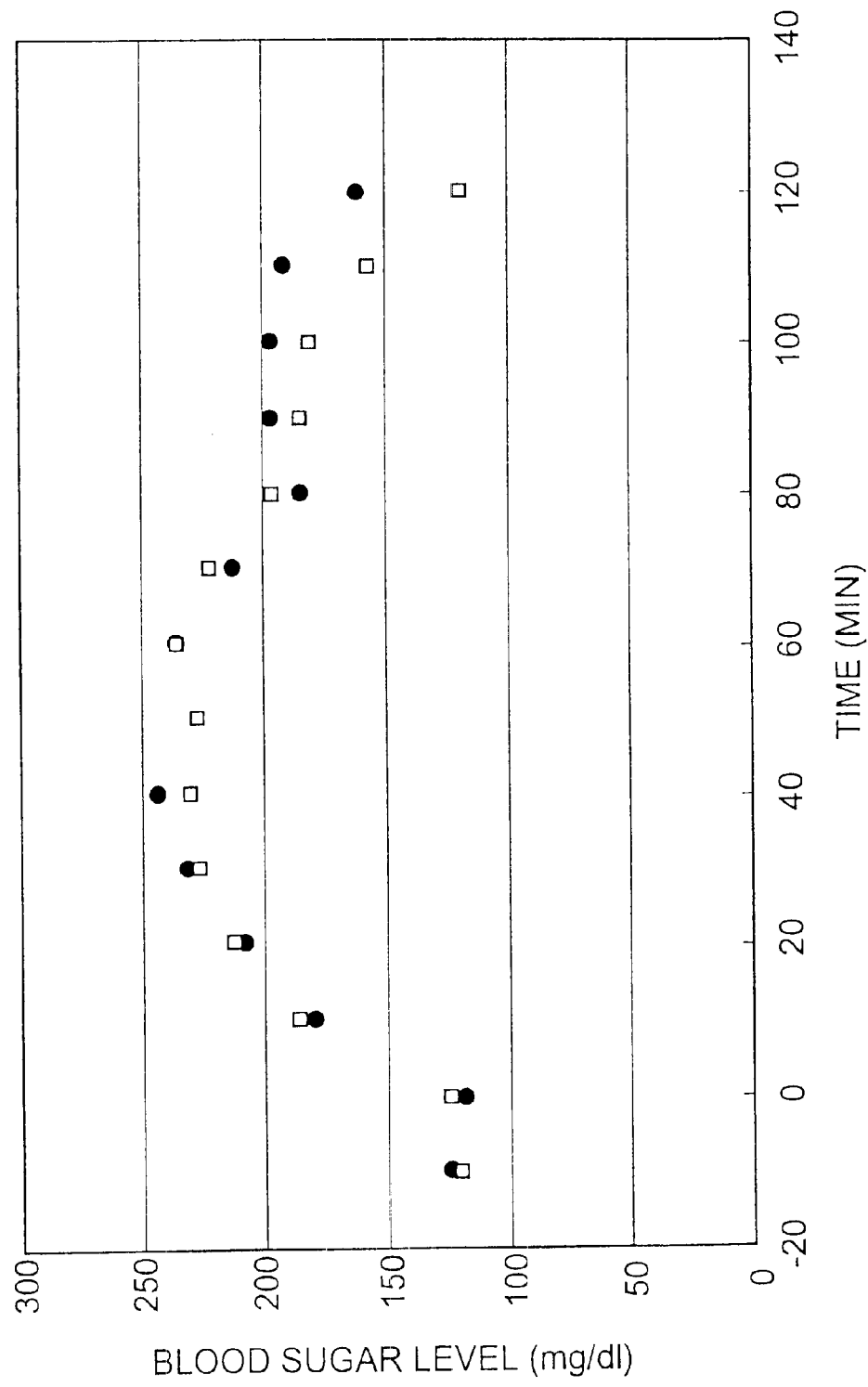
FIG. 3 is a graph which compares the respective variations over time of blood sugar levels following the ingestion of a saccharine liquid seen in a case where the present measurement site holder was used and a case where a universally known finger holder was used.

FIG. 3 is a graph which compares changes over time in the blood sugar levels following the ingestion of the abovementioned saccharine liquid that were measured using this measurement site holder with those that were measured using the abovementioned universally known finger holder. As is indicated by the black circles in FIG. 3, the blood sugar levels that were measured for patients when the measurement site holder 3 was used fluctuated over a range of 114 to 244 mg/dl. Furthermore, the squares indicate the blood sugar levels that were measured for patients when the finger holder was used.

Figure 4A:
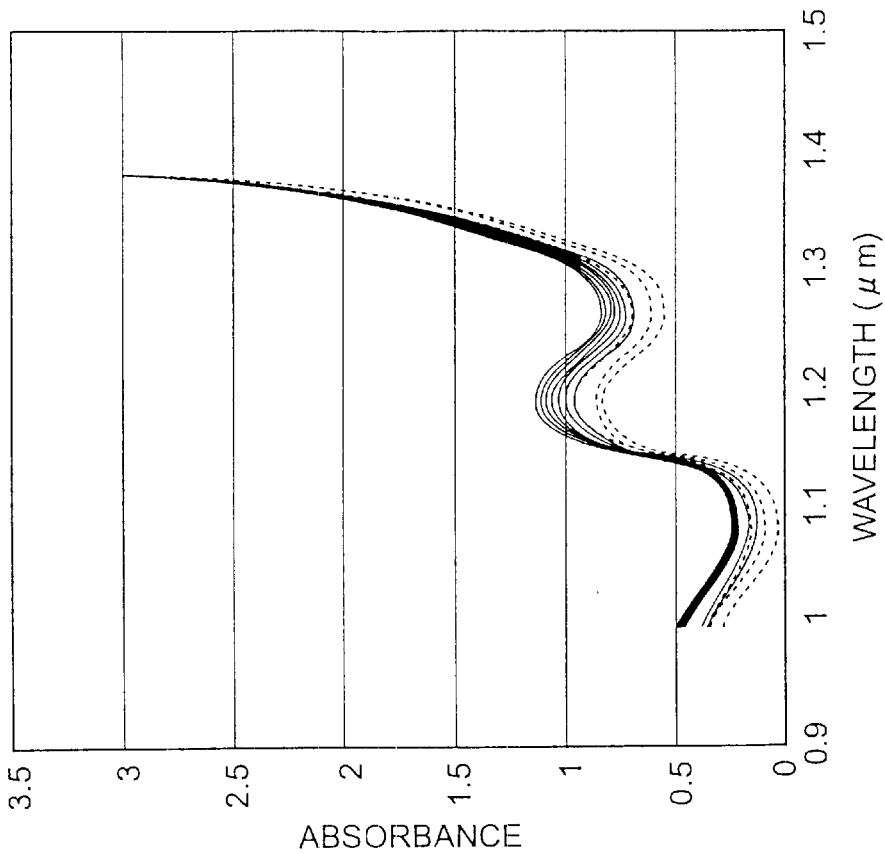
FIG. 4A is a graph which shows the near infrared spectrum (absorption characteristics) of the finger tip seen in a case where the measurement site holder of the present embodiment was used.
Figure 4B:
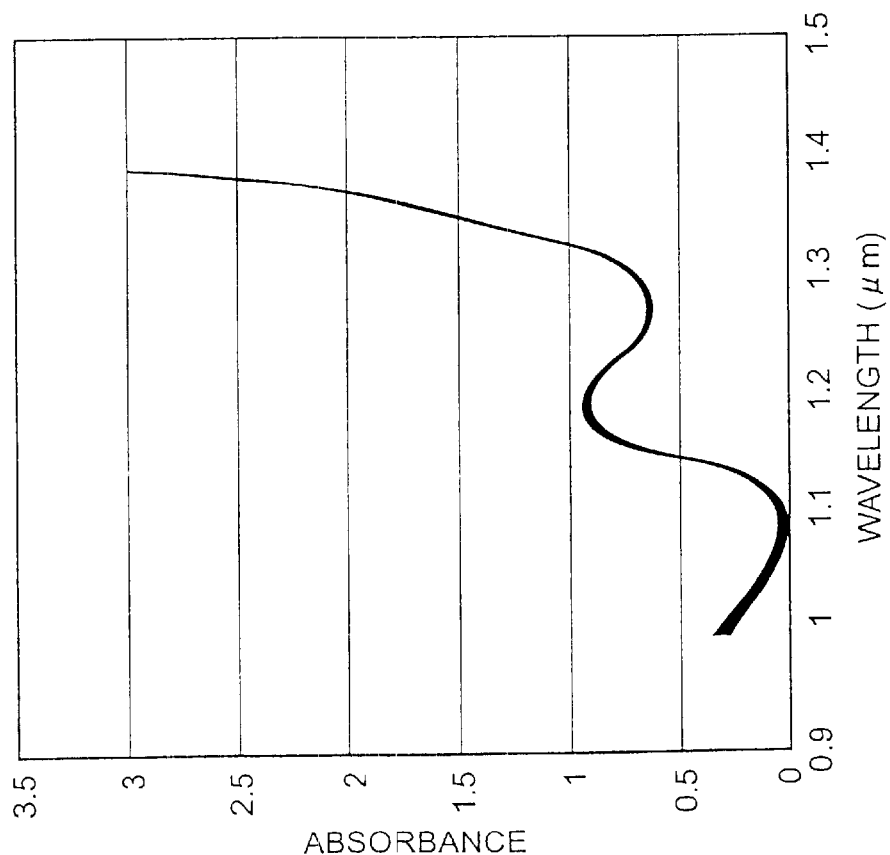
FIG. 4B is a graph which shows the near infrared spectrum (absorption characteristics) of the finger tip seen in a case where an ordinary finger holder was used.

FIG. 4A is a graph which shows the near infrared spectrum (absorption characteristics) of the finger tips measured using the measurement site holder of the present embodiment. FIG. 4B is a graph which shows the near infrared spectrum (absorption characteristics) of the finger tips measured using the abovementioned ordinary finger holder. The fluctuation in the spectrum seen in individual measurements of the near infrared spectrum measured using the measurement site holder 3 (see FIG. 4A) is conspicuously smaller than the fluctuation in the spectrum seen in individual measurements of the near infrared spectrum measuring using the finger holder (see FIG. 4B).

As a result of PLS regression analysis using cross validation, the correlation coefficient between the analysis values obtained by blood collection and the predicted values according to the near infrared spectrum was 0.85, and the root mean square error of prediction (RMSEP) was 23 mg/dl, in cases where the measurement site holder 3 was used. On the other hand, when the finger holder was used, the correlation coefficient between the analysis values obtained by blood collection and the predicted values according to the near infrared spectrum was 0.57, and the root mean square error of prediction was 41 mg/dl.

Specifically, it was confirmed that blood sugar levels can be quantitatively measured with a high degree of precision by using the measurement site holder 3 of the present embodiment.

Second Embodiment

Figure 5A:
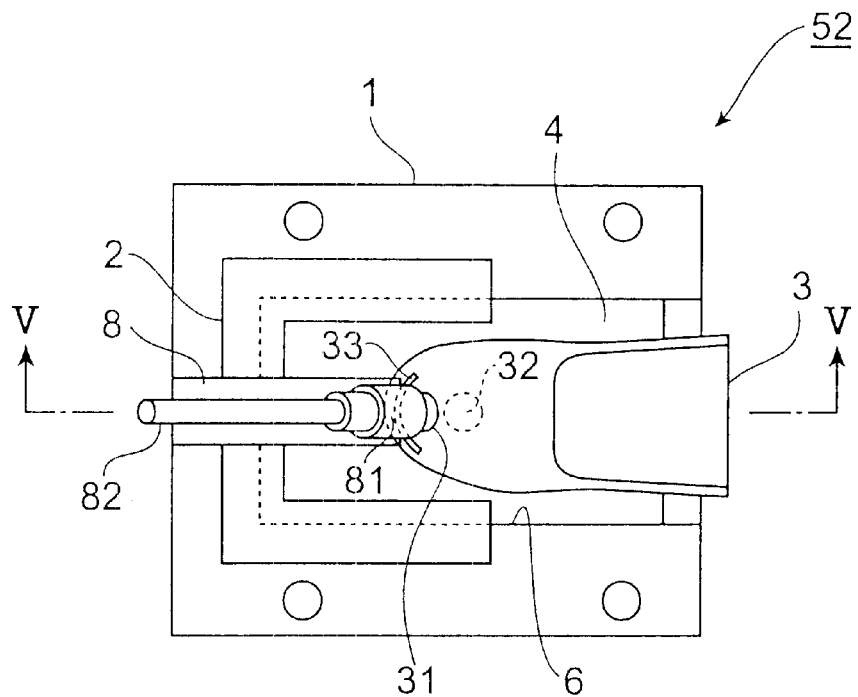
FIG. 5A is a plan view of the measurement site holding device of a noninvasive optical bioinstrumentation device constituting a second embodiment of the present invention.

FIG. 5A is a plan view of the measurement site holding device of a noninvasive optical bioinstrumentation device constituting a second embodiment of the present invention.

Figure 5B:
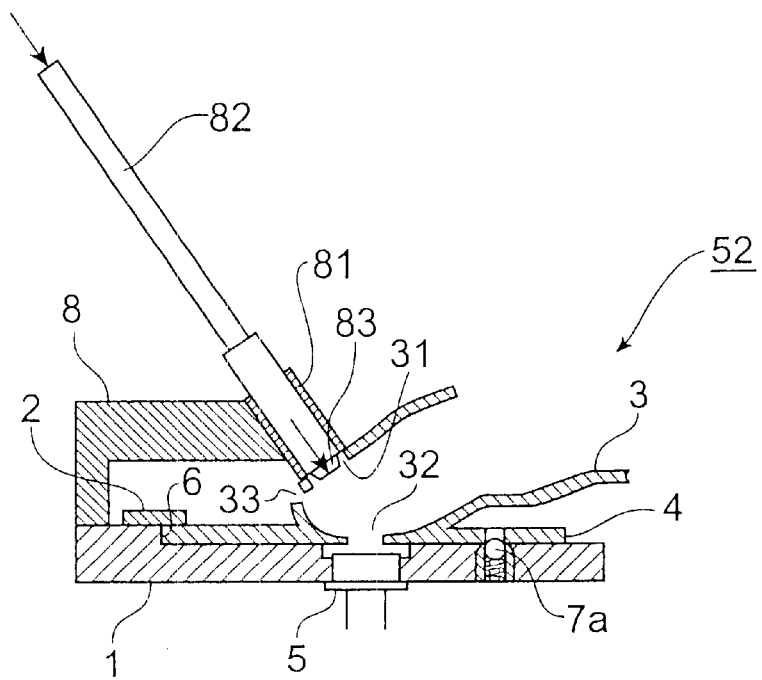
FIG. 5B is a sectional view along line V—V of the device shown in FIG. 5A.

FIG. 5B is a sectional view along line V—V of the device shown in FIG. 5A.

This second embodiment differs from the first embodiment in that this embodiment is constructed so that the finger 10 is illuminated by guiding the illuminating light with an optical fiber 82. Specifically, the measurement site holding device 52 of this second embodiment is further equipped with an optical fiber supporting base 8 which is disposed on the end portion of the base 1 located on the opposite side from the side where the base plate 4 is inserted, and which has a shape that extends from this end portion and covers the light-illumination opening part 31 of the measurement site holder 3 from above. Furthermore, the measurement site holding device 52 is also equipped with a guide 81 which is located on this optical fiber supporting base 8 in a position corresponding to the light-illumination opening part 31 of the abovementioned measurement site holder 3, and which has an inclined shape that is coaxial with the abovementioned light-illumination opening part 31. The tip end portion of the optical fiber 82 that is used to illuminate the finger 10 is inserted into this guide 81 so that the optical fiber 82 can slide.

In the measurement site holding device 52 constructed as described above, the emitting end 83 of the optical fiber 82 can always be accurately positioned inside the light-illumination opening part 31 by sliding the optical fiber 82, even if a measurement site holder 3 which has a different size (because of the size of the patient's finger) is mounted on the base 1 and the finger 10 is placed in this measurement site holder 3.

Accordingly, in this second embodiment, in addition to the effects of the first embodiment, variation in the measured values is greatly reduced regardless of the size of the patient's finger, so that blood sugar levels can be quantitatively measured with an even higher degree of precision.

Furthermore, it would also be possible to install an optical fiber that guides the light transmitted through the finger 10 to the photo-detection system in the installation position of the photo-detector 5. Furthermore, in cases where optical fibers are thus used in both locations, the light-illumination opening part 31 and the optical fiber on the side of this light-illumination opening part 31 can also be used for light detection, and the light-detection opening part 32 and the optical fiber on the side of this light-detection opening part 32 can also be used for light illumination.

Third Embodiment

Figure 6:
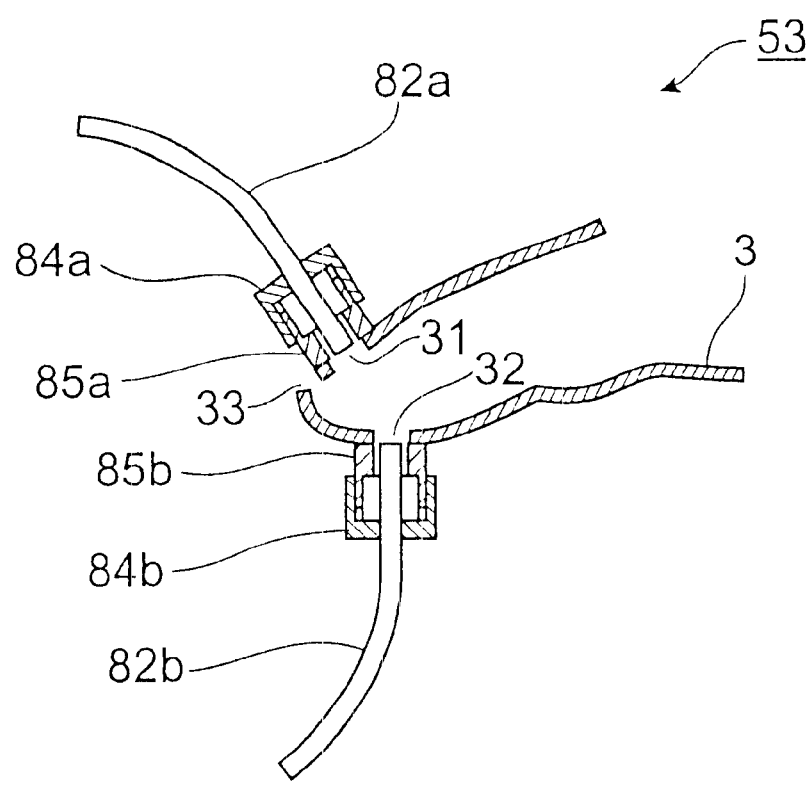
FIG. 6 is sectional view of the measurement site holding device of a noninvasive optical bioinstrumentation device constituting a third embodiment of the present invention.

FIG. 6 is a sectional view which shows the measurement site holding device of a noninvasive optical bioinstrumentation device constituting a third embodiment of the present invention.

This third embodiment differs from the first embodiment in the following respects: specifically, the finger 10 is illuminated by guiding the illuminating light with an optical fiber 82a, and the light transmitted through the finger 10 is guided into the photo-detection system by an optical fiber 82b; furthermore, the device is constructed so that these light transmitting and receiving optical fibers 82a and 82b are detachable from the measurement site holder 3.

Specifically, the measurement site holding device 53 of this third embodiment is equipped with an optical fiber receiving fitting 85a which has a tubular shape and which surrounds the light-illumination opening part 31, and an optical fiber receiving fitting 85b which has a tubular shape and which surrounds the light-detection opening part 32, on the outer surface of the measurement site holder 3. Furthermore, the measurement site holding device 53 is equipped with an optical fiber retaining fitting 84a which mounts the optical fiber 82a that is used to illuminate the finger 10, and which is detachably mounted on the optical fiber receiving fitting 85a, and an optical fiber retaining fitting 84b which mounts the optical fiber 82b that is used to guide the light transmitted through the finger 10 to the photo-detection system, and which is detachably mounted on the optical fiber receiving fitting 85b.

Various constructions may be used as concrete constructions that allow these optical fiber retaining fittings 84a and 84b to be respectively attached to or detached from the optical fiber receiving fittings 85a and 85b; for example, screws that are screw-engaged with each other or grooves and protruding parts that engage with each other may be used.

Furthermore, the device is constructed so that the light-illumination opening part 31, optical fiber receiving fitting 85a, optical fiber retaining fitting 84a and optical fiber 82a are coaxially positioned, and so that the light-detection opening part 32, optical fiber receiving fitting 85b, optical fiber retaining fitting 84b and optical fiber 82b are coaxially positioned. Furthermore, the optical fiber receiving fittings 85a and 85b, and the optical fiber retaining fittings 84a and 84b, are constructed so that these respective fittings have the same shape.

It goes without saying that the same effects as those obtained in the first embodiment can also be obtained in this construction; in addition, since the transmission and reception of light to and from the finger 10 are performed using optical fibers 82a and 82b, measurements can be performed on patients in locations that are separated from the main body side of the noninvasive optical bioinstrumentation device 50.

Furthermore, a construction may also be used in which a photo-detector which has a housing that is detachable from the measurement site holder 3 is mounted on the light-detection opening part 32 of this measurement site holder 3, so that light can be detected by this photo-detector via the light-detection opening part 32.

Furthermore, a construction may also be used in which a light-emitting element which has a housing that is detachable from the measurement site holder 3 is mounted on the light-illumination opening part 31 of this measurement site holder 3, so that light illumination can be performed by this light-emitting element via the light-illumination opening part 31.

Furthermore, as in the second embodiment, the light-illumination opening part 31 and the optical fiber 82a on the side of this light-illumination opening part 31 can also be used for light detection, and the light-detection opening part 32 and the optical fiber 82b on the side of this light-detection opening part 32 can also be used for light illumination.

Fourth Embodiment

Figure 7:
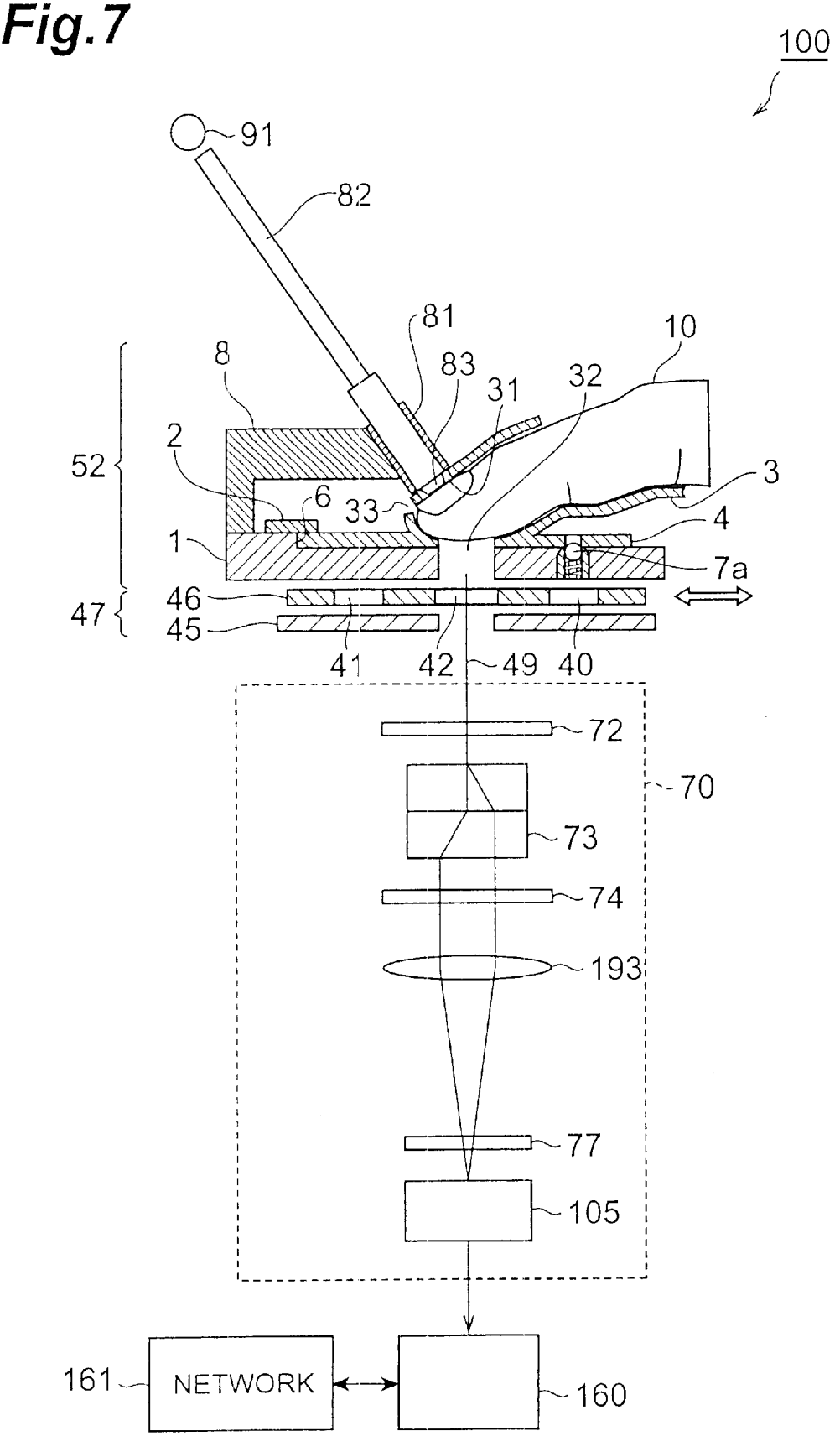
FIG. 7 is a schematic structural diagram of a noninvasive optical bioinstrumentation device constituting a fourth embodiment of the present invention.

FIG. 7 is a schematic structural diagram which illustrates a noninvasive optical bioinstrumentation device 100 constituting a fourth embodiment of the present invention. The noninvasive optical bioinstrumentation device 100 of this embodiment differs from the noninvasive optical bioinstrumentation device of the second embodiment in that a birefringent interferometer (photo-detection system) 70 is installed instead of the Michaelson interferometer 92 and photo-detector 5, and a computer 160 which has the functions of both the computer system part 94 and computer 60 is installed instead of these two parts. Furthermore, a sliding type turret 47 is installed as light adjustment means between the birefringent interferometer 70 and the light-detection opening part 32 side of the measurement site holding device 52.

The birefringent interferometer 70 is equipped with a polarizer 72 which polarizes the transmitted light that is transmitted through the finger 10, a Savart plate (polarized light splitting birefringent element) 73 which splits the transmitted light polarized by the polarizer 72 into polarized light with mutually perpendicular vibrational planes, thus producing parallel split light beams, an analyzer 74 which polarizes the split light split by the Savart plate 73, a converging lens (converging means) 193 and cylindrical lens 77 which cause the light polarized by the analyzer 74 to converge, thus forming an interferogram, and a solid state imaging element (photo-detector) 105 which detects the interferogram thus formed. This birefringent interferometer 70 acquires interferograms by causing interference of the transmitted light from the finger 10.

The computer 160 calculates the spectrum and concentrations of components in the living body on the basis of the interferograms acquired by the birefringent interferometer 70.

The sliding type turret 47 is disposed on the light-detection opening part 32 side of the measurement site holding device 52, and is equipped with a sliding plate 46 which consists of a light-blocking plate 40, aperture plate 41 and light-reducing plate 42 that are respectively separated from each other, and which can slide so that these respective plates coincide with the light-detection opening part 32, and a sliding plate guide 45 which holds the sliding plate 46 so that this sliding plate 46 can slide. This sliding type turret 47 reduces or narrows down light on the light path 49 of the transmitted light from the finger 10 by positioning the respective plates in this light path 49.

Next, the operation of the noninvasive optical bioinstrumentation device 100 of the present embodiment will be described.

First, the base plate 4 holding the measurement site holder (measurement site holder for the individual patient) 3 that has been manufactured for the patient that is the object of measurement in the same manner as in the first embodiment is mounted on the base 1. In this case, the measurement site holder 3 on the base plate 4 is mounted while being positioned with a high degree of precision with respect to the base 1 by means of the abovementioned groove 6, base plate supporting part 2, stopper 7a and the like.

Next, in a state in which the finger 10 has not been inserted into the measurement site holder 3, the sliding plate 46 of the sliding type turret 47 is caused to slide so that the light-blocking plate 40 is aligned with the light path 49. Then, in this state, background light data is acquired by means of the solid state imaging element 105.

Next, the polarization directions of the polarizer 72 and analyzer 74 of the birefringent interferometer 70 are set parallel to each other, and the sliding plate 46 is caused to slide so that the aperture plate 41 is aligned with the light path 49, and light is emitted from the light source 91. This light emitted from the light source passes through the optical fiber 82, light-illumination opening part 31 and interior of the measurement site holder 3, and is emitted from the light-detection opening part 32. The light is then narrowped down by the aperture plate 41 of the sliding type turret 47, and enters the birefringent interferometer 70.

The direction of polarization of the light that has entered the birefringent interferometer 70 is adjusted by the polarizer 72, and is split into two parallel light beams that are polarized in mutually perpendicular directions by the Savart plate 73. The directions of polarization of the split light beams are then again adjusted by the analyzer 74, so that the light beams are caused to interfere with each other. The interfering light is focused as an image on the solid state imaging element 105 by the converging lens 193 and cylindrical lens 77, so that a spatial interferogram is formed. The interferogram thus formed is detected by the solid state imaging element 105, and is acquired by the computer 160.

Next, the directions of polarization of the polarizer 72 and analyzer 74 of the birefringent interferometer 70 are set perpendicular to each other, and another interferogram is similarly acquired.

Then, the difference between the two spatial interferograms, i.e., the interferogram obtained with the directions of polarization of the polarizer 72 and analyzer 74 of the birefringent interferometer 70 set parallel to each other, and the interferogram obtained with these directions of polarization set perpendicular to each other, is taken by the computer 160. These two interferograms share a background component that is characteristic of the device, but have spatial interferogram components based on the transmitted light that are in a state in which light and dark are inverted.

Accordingly, if the difference between the two interferograms is taken, the background component is eliminated, and the spatial interferogram intensity based on the light from the measurement site holder 3 is doubled, so that the S/N ratio of the interferogram can be improved. Furthermore, the interferogram whose S/N ratio has thus been improved is analyzed by the computer 160 and acquired as reference data.

Next, the patient inserts the finger 10 used in the preparation of the negative impression into the measurement site holder 3. Furthermore, the sliding plate 46 of the sliding type turret 47 is caused to slide so that a state is obtained in which nothing blocks the light path 49, and light from the light source 91 is caused to be incident on a specified position of the finger 10 via the optical fiber 82. The transmitted light that passes through the finger enters the birefringent interferometer 70 via the light-detection opening part 32, and an interferogram is formed on the solid state imaging element 105 by the same operation as that described above. This interferogram is detected by the solid state imaging element 105, and is acquired by the computer 160.

In this case, in order to maximize the S/N ratio of the detected light detected by the solid state imaging element 105, the amount of light is adjusted if necessary by causing the sliding plate 46 of the sliding type turret 47 to slide so that the light-reducing plate 42 is aligned with the light path 49. Furthermore, in this case as well, two interferograms, i.e., an interferogram obtained with the directions of polarization of the polarizer 72 and analyzer 74 of the birefringent interferometer 70 set perpendicular to each other, and an interferogram obtained with these directions of polarization set parallel to each other, are acquired in the same manner as described above, and the difference is taken so that an interferogram based on the transmitted light is acquired with an improved S/N ratio.

Then, the computer 160 acquires an interferogram based on the transmitted light, a reference spectrum obtained beforehand and a near infrared spectrum based on the background light data, and prepares a working curve for the blood sugar levels on the basis of this near infrared spectral data and the blood sugar levels obtained by blood collection performed at the same time as the measurement of the near infrared spectrum. Then, as in the first embodiment, the computer 160 obtains blood sugar levels by comparing the measured near infrared spectrum with this working curve.

Thus, the noninvasive optical bioinstrumentation device 100 of the present embodiment makes it possible to obtain the same effects as those of the noninvasive optical bioinstrumentation device of the second embodiment; furthermore, since interferograms are obtained by polarizing and causing interference of the transmitted light by means of a birefringent interferometer 70, the required construction is simpler than that of the noninvasive optical bioinstrumentation device of the second embodiment using a Michelson interferometer 92, since mirror driving or control mechanism, and no mechanical driving parts for a laser interferometer or the like used for sampling designation of the main interferometer. Accordingly, a reduction in size and weight and an improvement of the vibration resistance can be achieved.

Furthermore, as a result, a noninvasive optical bioinstrumentation device 100 which offers high portability and high precision can be obtained at a low cost.

Furthermore, by taking the difference between an interferogram obtained with the directions of polarization of the polarizer 72 and analyzer 74 set perpendicular to each other and an interferogram obtained with the directions of polarization of the polarizer 72 and analyzer 74 set parallel to each other, it is possible to eliminate the background component and double the intensity of the interferogram, so that the S/N ratio can be increased even further. Accordingly, blood sugar levels or the like can be quantitatively determined with an even higher degree of precision.

Furthermore, since a sliding type turret 47 is installed so that the light that is incident on the birefringent interferometer can easily be narrowped down or reduced, interferograms with a high S/N ratio can be acquired.

Furthermore, since spatial interferograms are caused to converge on the solid state imaging element 105 by means of a cylindrical lens 77, the spatial interferogram intensity can be further increased, so that the S/N ratio is improved to an even greater degree.

Here, in order to confirm the abovementioned effects of the noninvasive optical bioinstrumentation device 100 of the present embodiment, the present inventors measured the blood sugar levels of patients under the same conditions as in the first embodiment, using the procedure described above.

In the experiment, a tungsten halogen lamp (8 W) was used as the light source 91, infrared glass polarizing elements (1310HC manufactured by Corning Co.) were used as the polarizer 72 and analyzer 74, and a plate made of titanium oxide was used as the Savart plate 73. Furthermore, an InGaAs linear image sensor (G7231-256 manufactured by Hamamatsu Photonics K.K.), which is a multi-channel photo-detector, was used as the solid state imaging element 105, and the measurement wavelength range was set at 0.95 to 1.345 $\mu$m.

The results are compared with those obtained for the first embodiment in FIG. 8. The blood sugar levels fluctuated over a range of 109 to 225 mg/dl. Furthermore, when a PLS regression analysis was performed, the correlation coefficient between the measured blood sugar levels obtained by blood collection and the values predicted by the noninvasive optical bioinstrumentation device 100 of the present embodiment was 0.94, and the root mean square error of prediction (RMSEP) was 15 mg/dl. It was thus confirmed that the noninvasive optical bioinstrumentation device 100 of the fourth embodiment equipped with a birefringent interferometer 70 is superior to the noninvasive optical bioinstrumentation device 50 of the first embodiment equipped with a Michelson interferometer both in terms of the correlation coefficient and in terms of the root mean square error of prediction, so that the determinability of blood sugar levels is improved even further.

Fifth Embodiment

Figure 9:
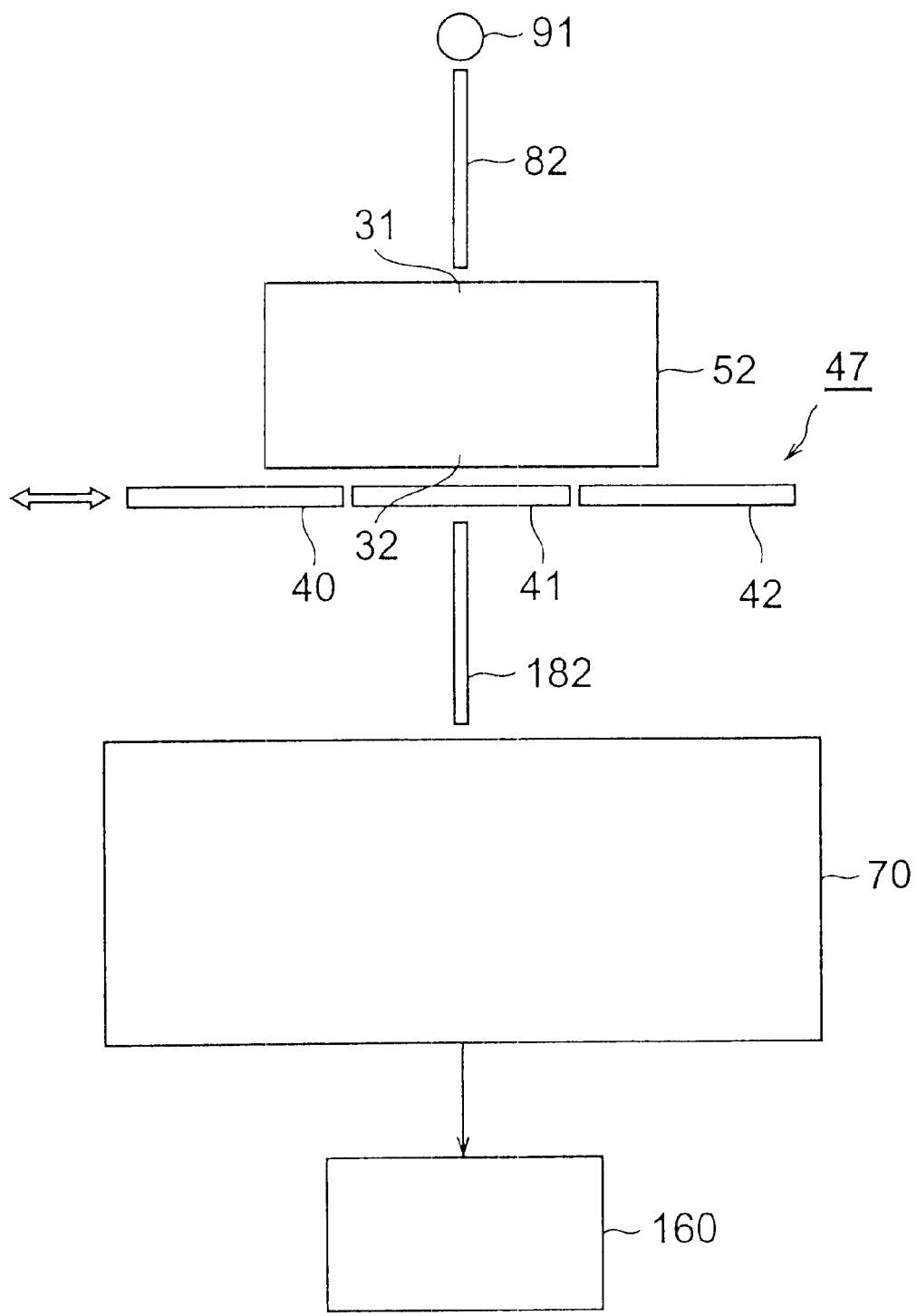
FIG. 9 is a schematic structural diagram of a noninvasive optical bioinstrumentation device constituting a fifth embodiment of the present invention.

Next, a fifth embodiment of the present invention will be described with reference to FIG. 9. This embodiment differs from the fourth embodiment in that an optical fiber 182 which conducts the light that has passed through the sliding type turret 47 to the birefringent interferometer 70 is provided. The same effects as those obtained in the fourth embodiment can be obtained in this embodiment as well; furthermore, measurement site holding device 52 can be installed in a location that is separated from the birefringent interferometer 70.

Sixth Embodiment

Figure 10:
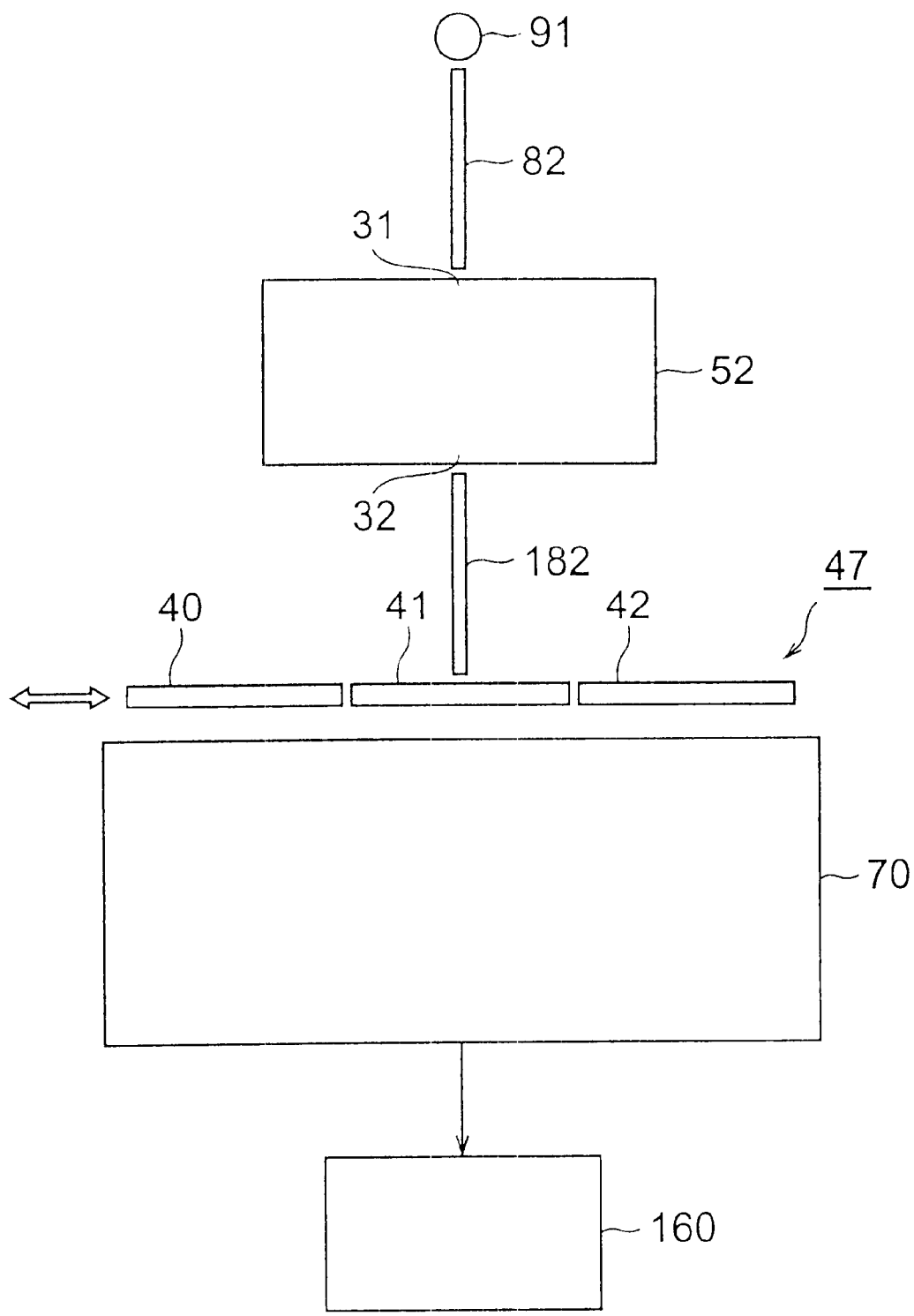
FIG. 10 is a schematic structural diagram of a noninvasive optical bioinstrumentation device constituting a sixth embodiment of the present invention.

Next, a sixth embodiment of the present invention will be described with reference to FIG. 10. This embodiment differs from the fifth embodiment in that the sliding type turret 47 is installed on the side of the birefringent interferometer 70 rather than on the side of the measurement site holding device 52, so that the light emitted from the light-detection opening part 32 of the measurement site holding device 52 is incident on the birefringent interferometer 70 after being incident on the sliding type turret 47 via the optical fiber 182. The same effects as those obtained in the fifth embodiment can also be obtained by means of this embodiment.

Seventh Embodiment

Figure 11:
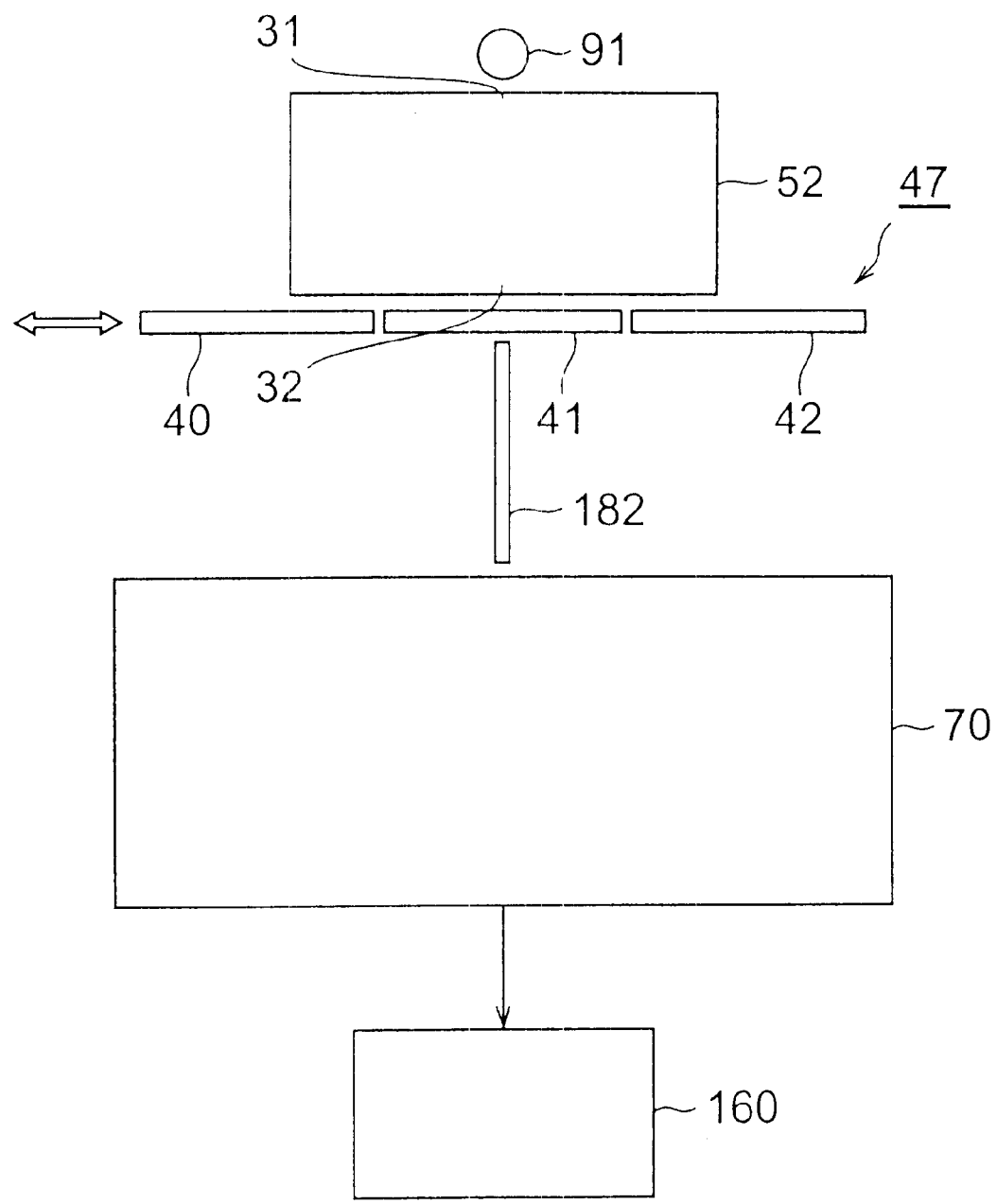
FIG. 11 is a schematic structural diagram of a noninvasive optical bioinstrumentation device constituting a seventh embodiment of the present invention.

Next, a seventh embodiment of the present invention will be described with reference to FIG. 11. This embodiment differs from the fifth embodiment in that the light source 91 is installed in the measurement site holding device 52 so that the illuminating light from the light source 91 is caused to illuminate the finger 10 directly. It goes without saying that the same effects as those obtained in the fifth embodiment can also be obtained by means of this embodiment.

Eighth Embodiment

Figure 12:
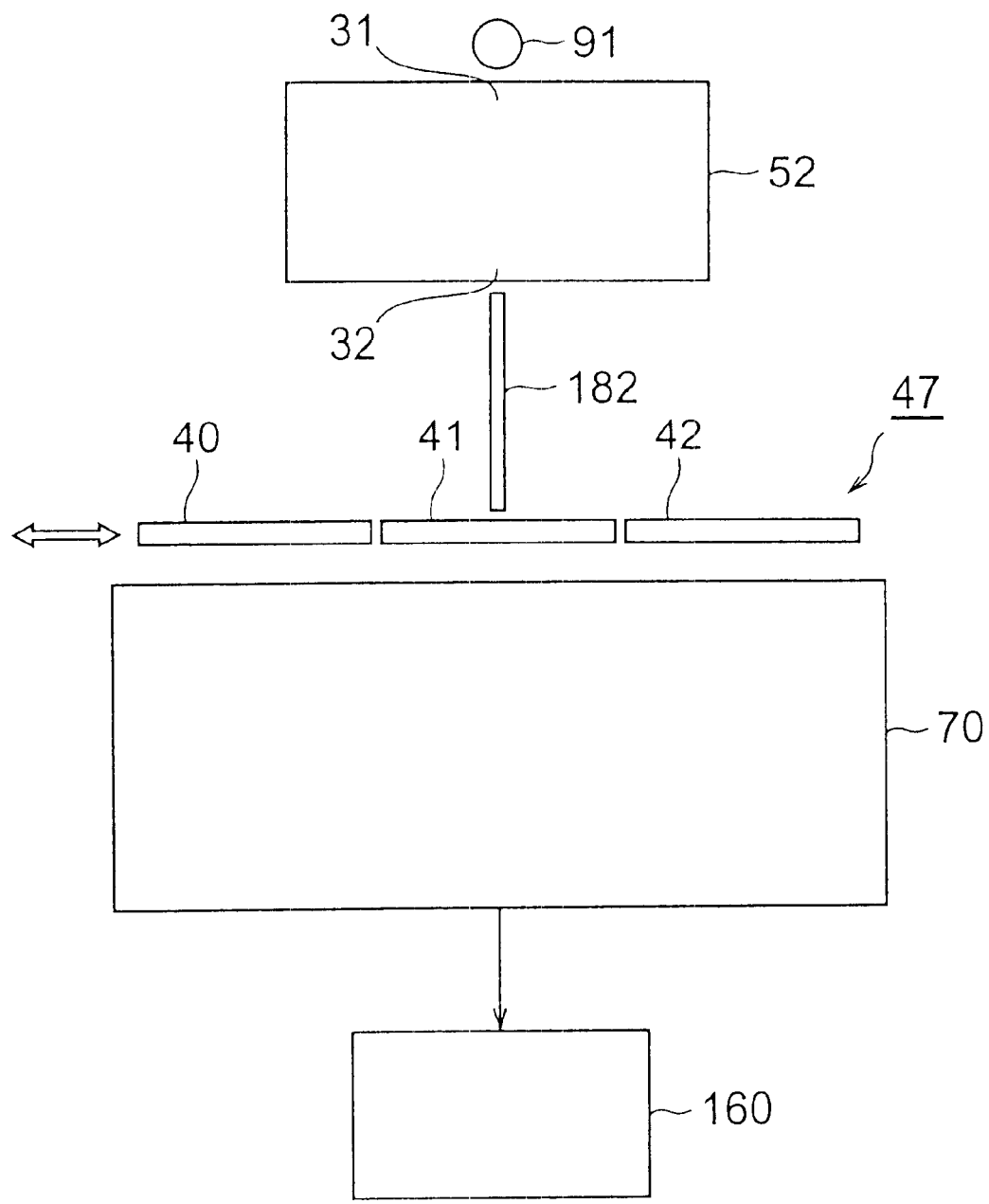
FIG. 12 is a schematic structural diagram of a noninvasive optical bioinstrumentation device constituting an eighth embodiment of the present invention.

Next, an eighth embodiment of the present invention will be described with reference to FIG. 12. This embodiment differs from the seventh embodiment in that the sliding type turret 47 is installed on the side of the birefringent interferometer 70 so that the light emitted from the light-detection opening part 32 of the measurement site holding device 52 is incident on the birefringent interferometer 70 after being incident on the sliding type turret 47 via the optical fiber 182. The same effects as those obtained in the seventh embodiment can also be obtained by means of this embodiment.

Ninth Embodiment

Figure 13:
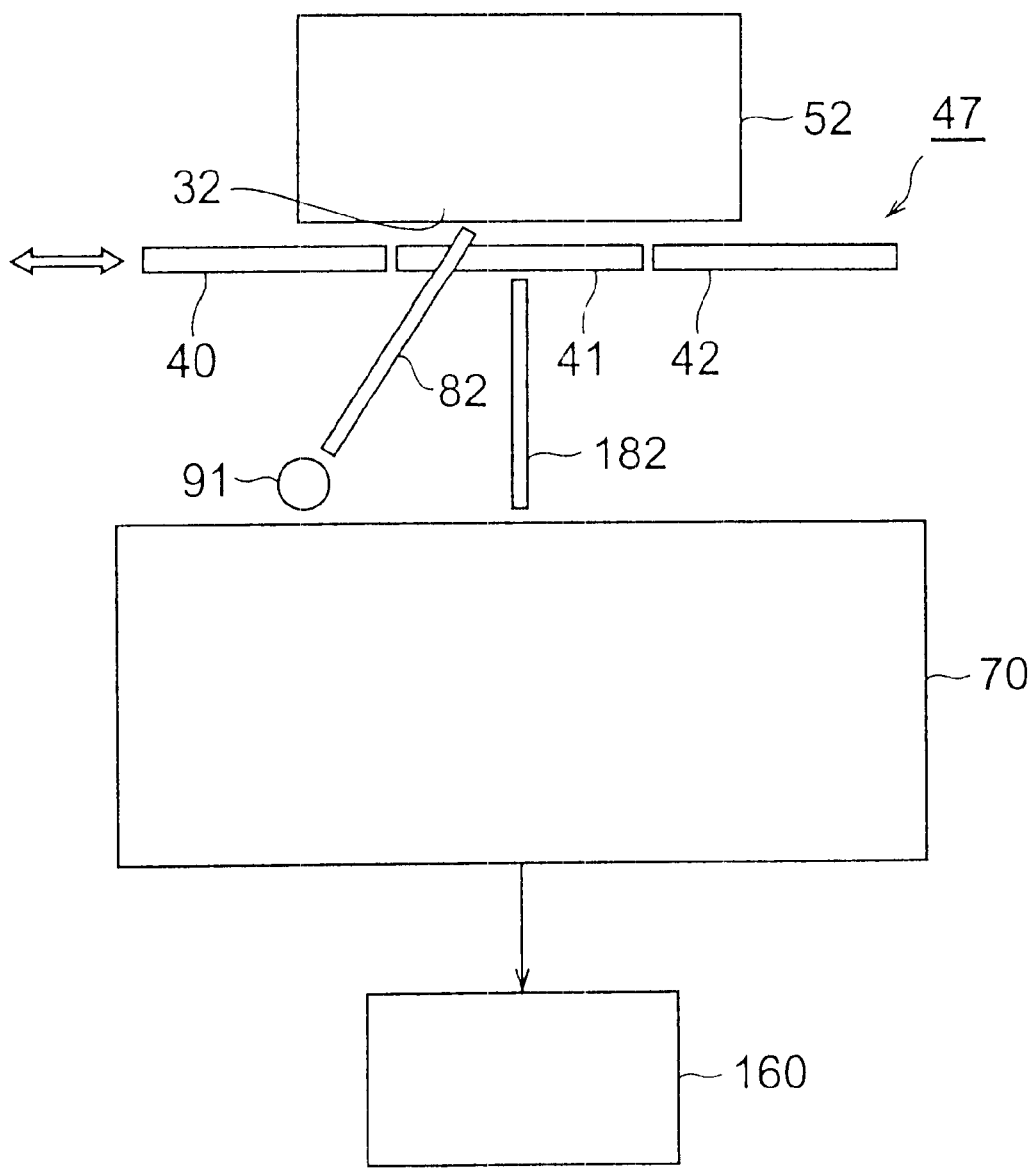
FIG. 13 is a schematic structural diagram of a noninvasive optical bioinstrumentation device constituting a ninth embodiment of the present invention.

Next, a ninth embodiment of the present invention will be described with reference to FIG. 13. This embodiment differs from the fifth embodiment in that an optical fiber 82 which conducts the illuminating light from the light source 91 to the finger 10 is connected to the side of the light-detection opening part 32 in order to cause diffused and reflected light from the finger 10 to be incident on the birefringent interferometer 70. Here, the light-detection opening part 32 is also used as a light-illumination opening part by means of the optical fiber 82. As a result, the illuminating light that is emitted from the light source 91 is caused to illuminate the finger 10 from the light-detection opening part 32 via the optical fiber 82, and the diffused and reflected light from the finger 10 is incident on the birefringent interferometer 70 via the light-detection opening part 32, sliding type turret 47 and optical fiber 182. Accordingly, the same effects as those obtained in the fifth embodiment can be obtained. Furthermore, it would also be possible to form a separate light-illumination opening part on the light-detection opening part 32 side of the measurement site holding device 52 (i.e., the lower side in the figure), and to connect the optical fiber 82 to this light-illumination opening part.

Tenth Embodiment

Figure 14:
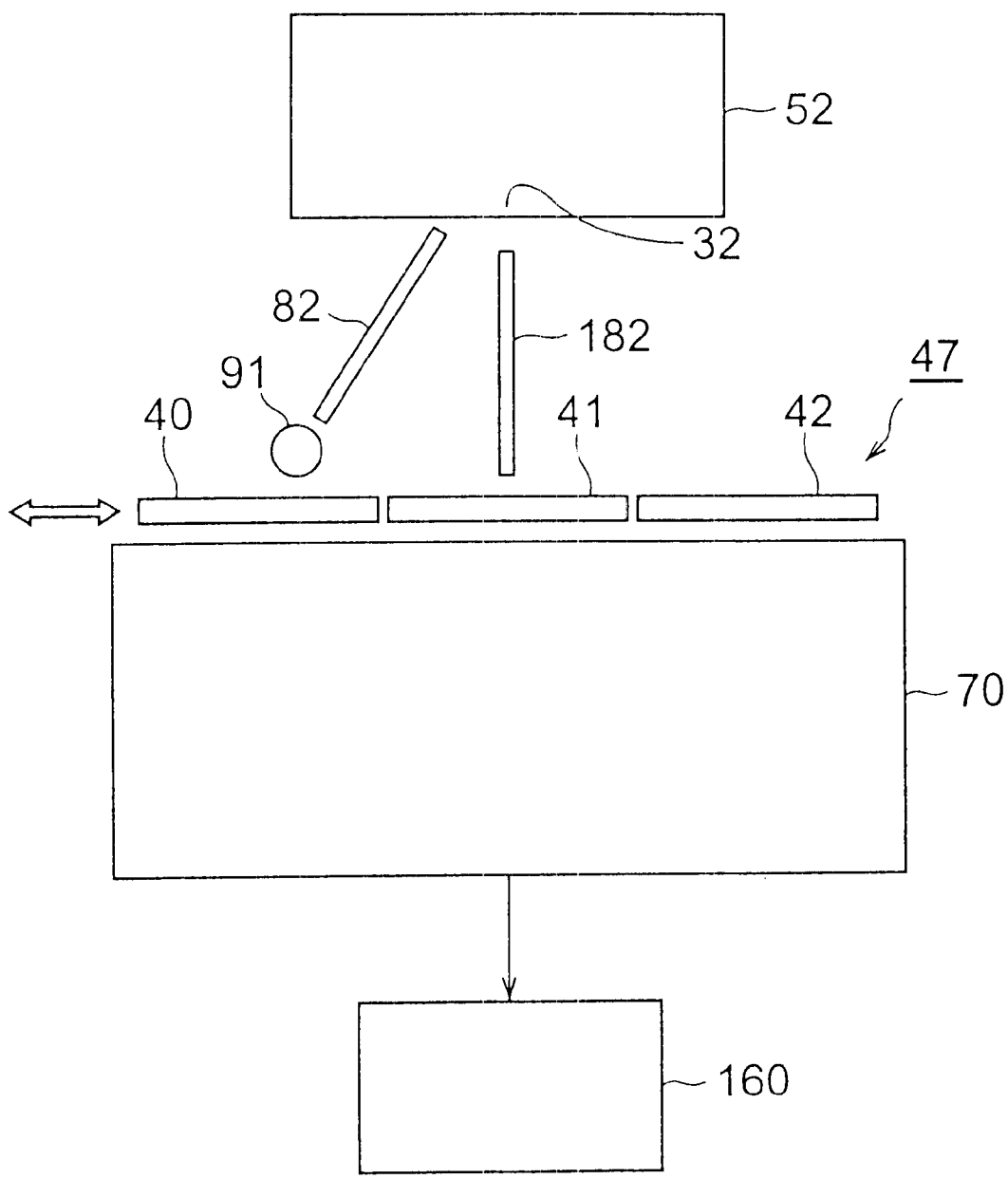
FIG. 14 is a schematic structural diagram of a noninvasive optical bioinstrumentation device constituting a tenth embodiment of the present invention.

Next, a tenth embodiment of the present invention will be described with reference to FIG. 14. This embodiment differs from the ninth embodiment in that the sliding type turret 47 is installed on the side of the birefringent interferometer 70, so that the diffused and reflected light emitted from the light-detection opening part 32 of the measurement site holding device 52 is incident on the birefringent interferometer 70 after being incident on the sliding type turret 47 via the optical fiber 182. The same effects as those obtained in the ninth embodiment can also be obtained by means of this embodiment.

Eleventh Embodiment

Figure 15:
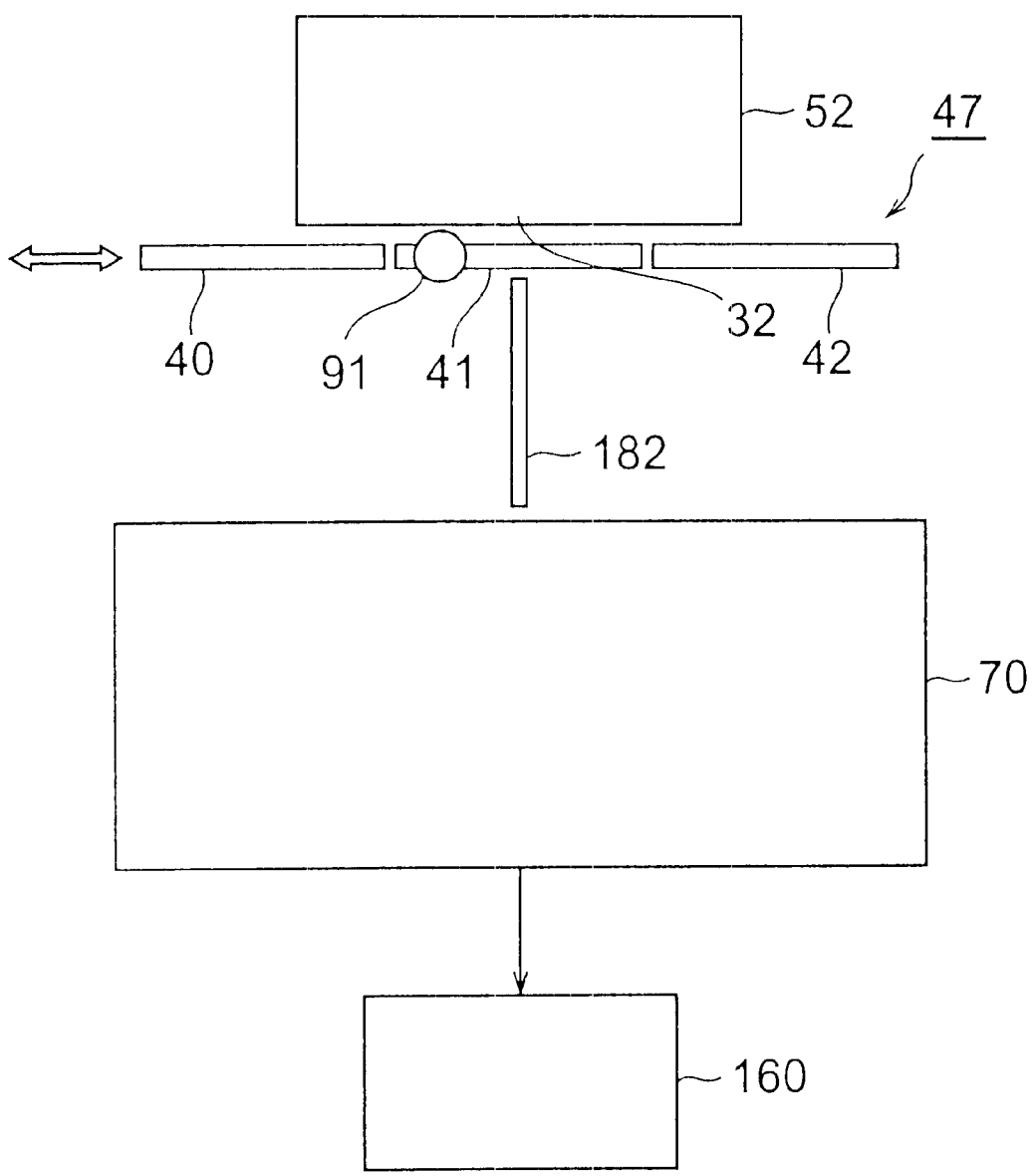
FIG. 15 is a schematic structural diagram of a noninvasive optical bioinstrumentation device constituting an eleventh embodiment of the present invention.

Next, an eleventh embodiment of the present invention will be described with reference to FIG. 15. This embodiment differs from the ninth embodiment in that the light source 91 is installed on the light-detection opening part 32 side of the measurement site holding device 52, so that the illuminating light from the light source 91 is caused to illuminate the finger 10 directly. The same effects as those obtained in the ninth embodiment can also be obtained by means of this embodiment.

Twelfth Embodiment

Figure 16:
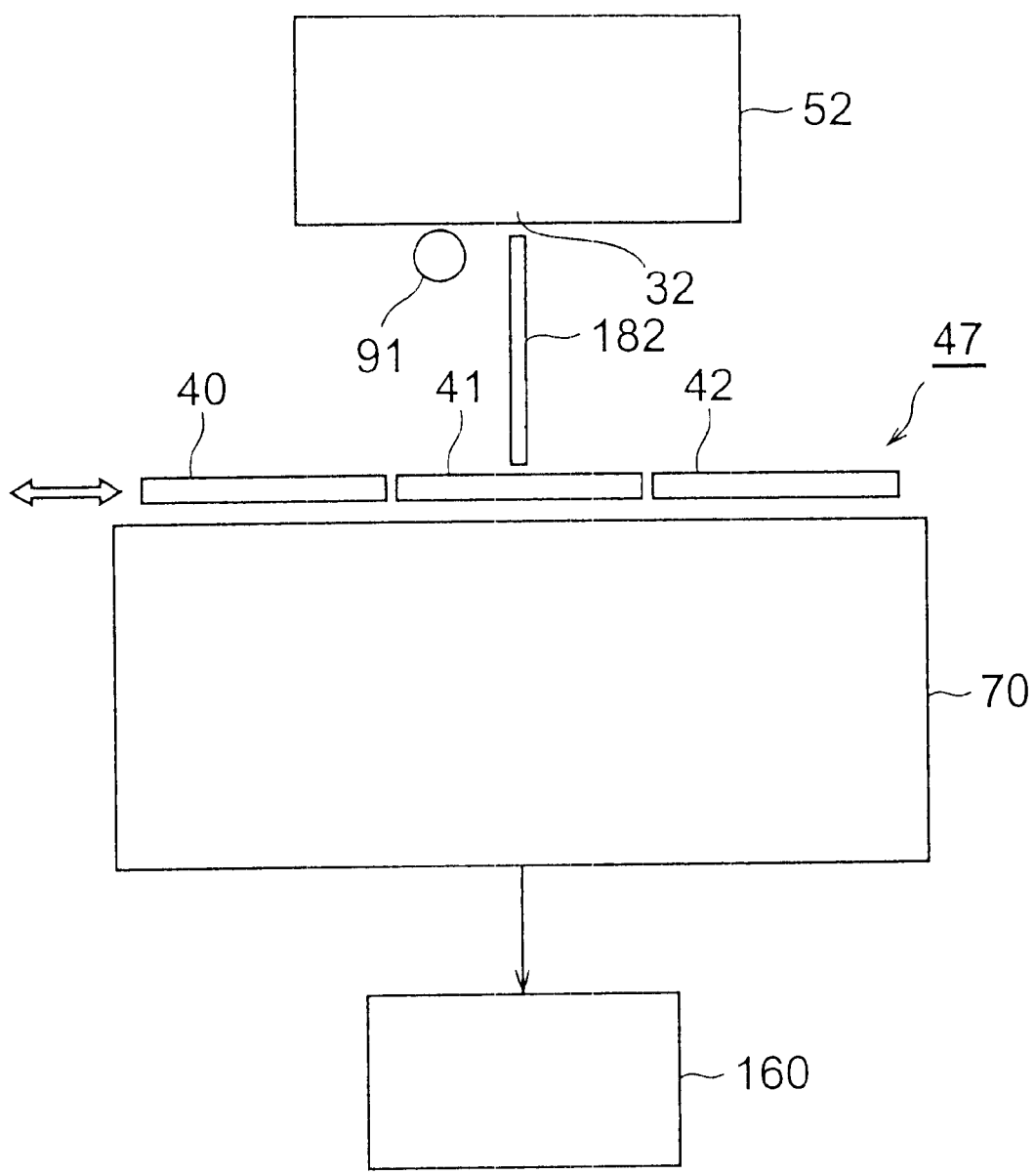
FIG. 16 is a schematic structural diagram of a noninvasive optical bioinstrumentation device constituting a twelfth embodiment of the present invention.

Next, a twelfth embodiment of the present invention will be described with reference to FIG. 16. This embodiment differs from the eleventh embodiment in that the sliding type turret 47 is installed on the side of the birefringent interferometer 70 rather than on the side of the measurement site holding device 52, so that the light emitted from the light-detection opening part 32 of the measurement site holding device 52 is incident on the birefringent interferometer 70 after being incident on the sliding type turret 47 via the optical fiber 182. The same effects as those obtained in the eleventh embodiment can also be obtained by means of this embodiment.

Thirteenth Embodiment

Next, a thirteenth embodiment of the present invention will be described with reference to FIG. 17.

Figure 17A:
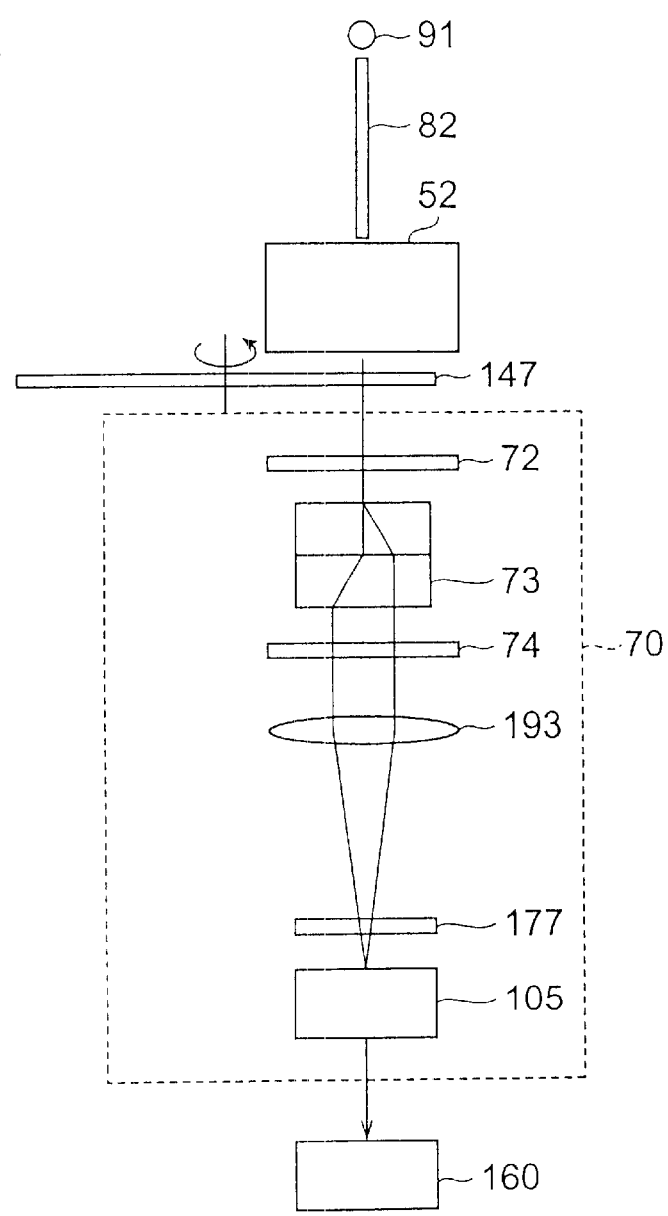
FIG. 17A is an overall schematic structural diagram of a noninvasive optical bioinstrumentation device constituting a thirteenth embodiment of the present invention.
Figure 17B:
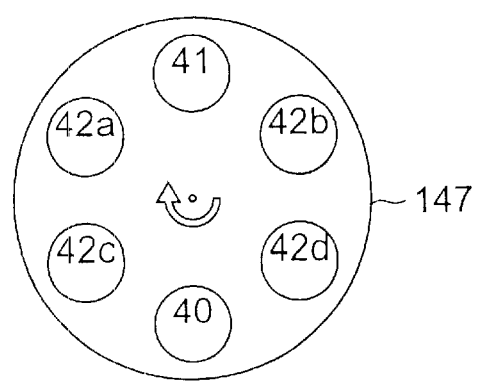
FIG. 17B is a front view of the circular turret shown in FIG. 17A.

FIG. 17A is an overall schematic structural diagram of a noninvasive optical bioinstrumentation device constituting a thirteenth embodiment of the present invention. FIG. 17B is a front view of the circular turret shown in FIG. 17A. As is shown in FIG. 17A, this embodiment differs from the fourth embodiment in that the device is equipped with a circular turret (light adjustment means) 147 instead of a sliding type turret 47. As is shown in FIG. 17B, this circular turret 147 has a light-blocking plate 40, an aperture plate 41 and a plurality of light-reducing plates 42a, 42b, 42c and 42d with different light reduction rates, which are installed on the circumference of the same circle.

Furthermore, the abovementioned light-blocking plate 40, aperture plate 41 and light-reducing plates 42a through 42d can be appropriately selected by rotating the circular turret 147, so that the same effects as those obtained in the fourth embodiment can be obtained. Furthermore, since a plurality of light-reducing plates 42a through 42d are provided, the light-reducing plate with the optimal light reduction rate can be selected; accordingly, optimization of the S/N ratio of the interferograms can be accomplished even more efficiently.

Fourteenth Embodiment

Figure 18:
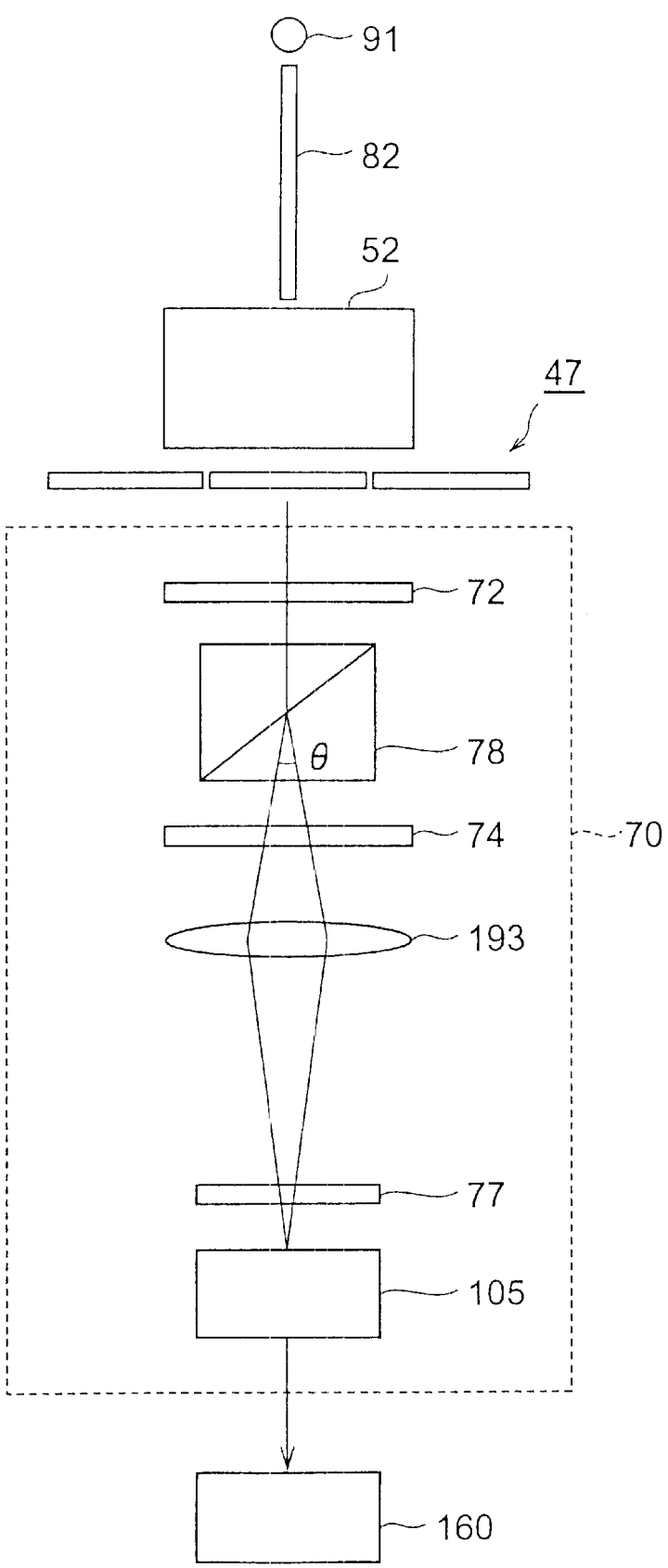
FIG. 18 is a schematic structural diagram of a noninvasive optical bioinstrumentation device constituting a fourteenth embodiment of the present invention.

Next, a fourteenth embodiment of the present invention will be described with reference to FIG. 18. This embodiment differs from the fourth embodiment in that a Wollaston prism (polarized light splitting birefringent element) 78 is installed in the birefringent interferometer 70 instead of a Savart plate 73. The transmitted light that passes through the polarizer 72 is split into linearly polarized light beams that are perpendicular to each other by this Wollaston prism 78, and these beams are emitted at a separation angle of θ. Then, the two light beams thus emitted are polarized by the analyzer 74, and are caused to converge by the convergent lens 193 and cylindrical lens 77, so that an interferogram is formed on the solid state imaging element 105. As a result, the same effects as those obtained in the fourth embodiment can be obtained.

Fifteenth Embodiment

Figure 19:
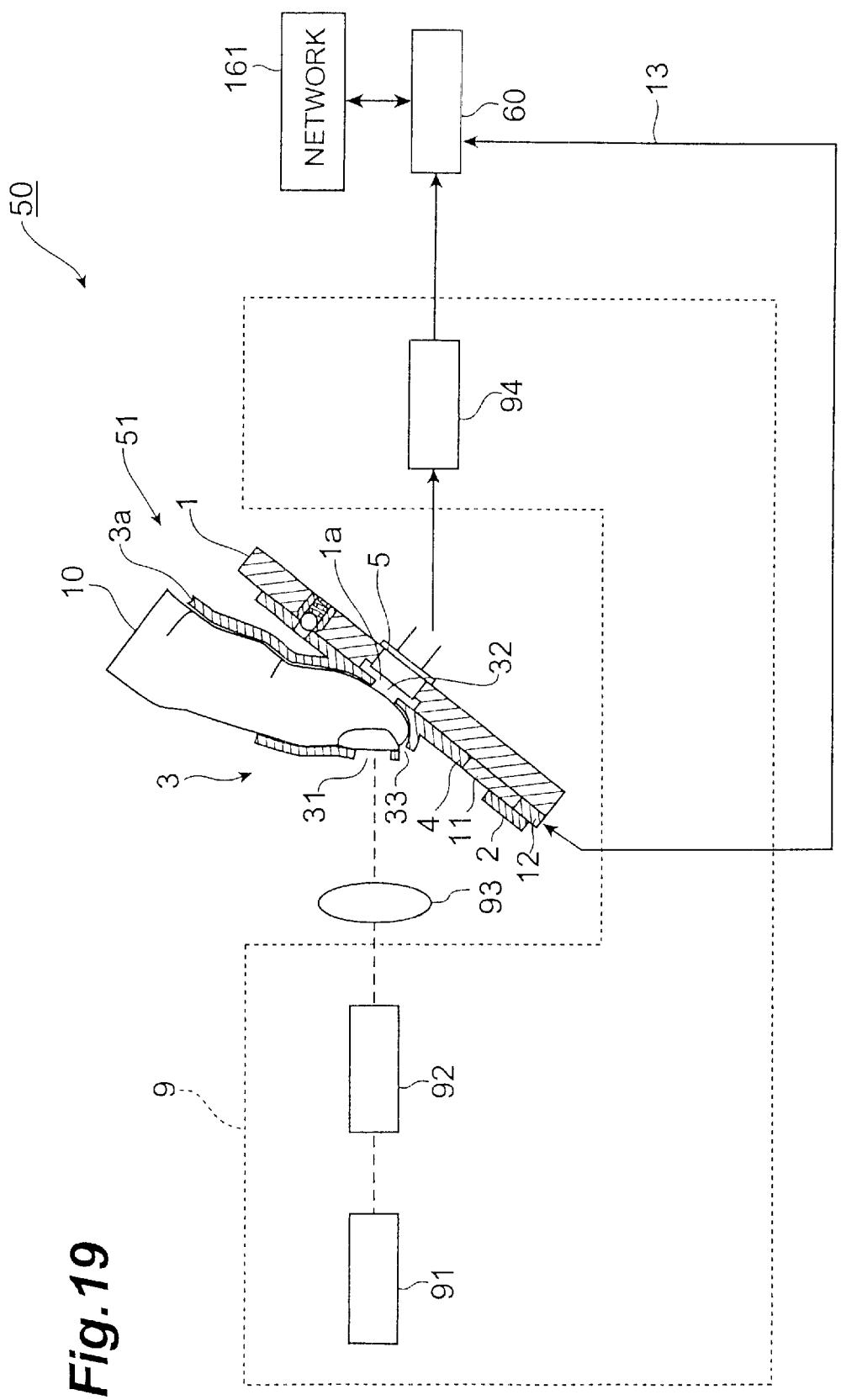
FIG. 19 is a schematic structural diagram showing a noninvasive optical bioinstrumentation device which mounts the measurement site holder of a noninvasive optical bioinstrumentation device constituting a fifteenth embodiment of the present invention.
Figure 20A:
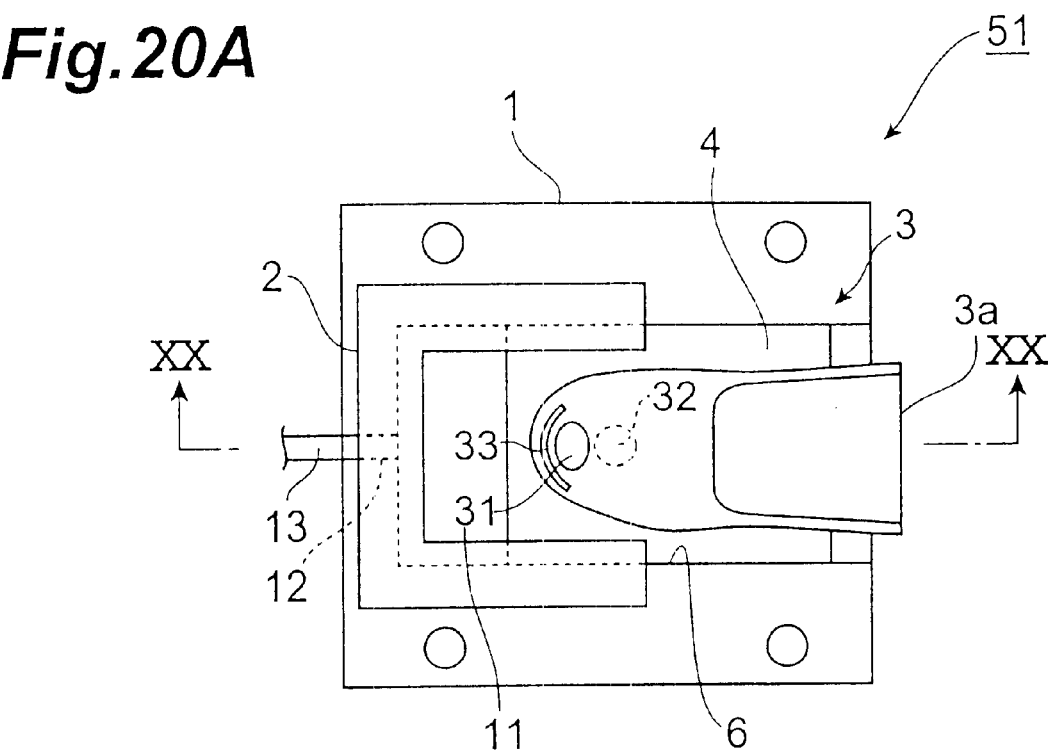
FIG. 20A is a plan view of a device shown with the measurement site holding device mounting the measurement site holder shown in FIG. 19 extracted.
Figure 20B:
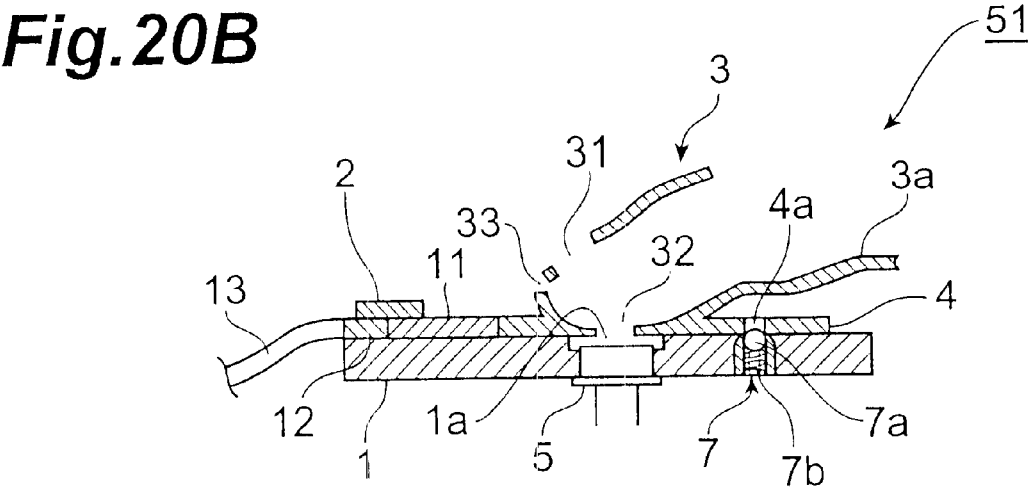
FIG. 20B is a sectional view along line XX—XX of the device shown in FIG. 20A.

FIG. 19 is a schematic structural diagram of a noninvasive optical bioinstrumentation device constituting a fifteenth embodiment of the present invention, FIG. 20A is a plan view of a device shown with the measurement site holding device mounting the measurement site holder shown in FIG. 19 extracted, and FIG. 20B is a sectional view along line XX—XX in FIG. 20A. Furthermore, since the same elements are labeled with the same symbols, a description of constructions that duplicate the abovementioned embodiments is omitted.

In addition to a main body part 3a, the measurement site holder 3 of the noninvasive optical bioinstrumentation device (measuring device) 50 of the present embodiment is equipped with a recording medium 11 that records various types of living-body information. When the recording medium 11 and base plate 4 of the measurement site holder 3 are inserted along the groove 6 from the open end of this groove 6, and the recording medium 11 is caused to abut the closed end portion of the groove 6, the spherical stopper 7a is inserted into an opening part 4a formed in the base plate 4, so that the measurement site holder 3 is positioned on the base 1 and is always fastened in the same position.

Furthermore, as is shown in FIG. 19, the device is constructed as follows: namely, a computer 60 is connected via a recording medium connecting connector 12 and recording medium connecting cable 13 to the recording medium 11 mounted on the measurement site holder 3, and working curves (living-body information) for individual patients acquired by this computer 60, as well as blood sugar levels (living-body information) or the like for individual patients determined using these working curves are recorded on this recording medium 11; furthermore, this living-body information is read out by the computer 60 as required.

Various types of media can be used as this recording medium 11; for example, the use of flash memory cards currently used as compact recording media in household devices and the like, Smart Media manufactured by Toshiba Corp., Compact Flash manufactured by SanDisk Corporation, Memory Stick manufactured by Sony Corp. or the like is desirable.

These media are available in large quantities as commercial products, and are thus easily obtained. Recently, furthermore, large-capacity media have also appeared, so that these media are suitable for use as the recording medium 11.

Next, the operation of a noninvasive optical bioinstrumentation device 50 equipped with a measurement site holder 3 constructed as described above will be described. First, the measurement site holder 3 for the exclusive use of the individual patient, which has been manufactured for the patient that is the object of measurement, is mounted on the base 1. In this case, the measurement site holder 3 is accurately positioned and mounted on the base 1 by means of the abovementioned groove 6, base plate supporting part 2, stopper 7a and the like.

Next, the patient places the finger 10 used in the preparation of the negative impression inside the main body part 3a of the measurement site holder 3. In this case, since the main body part 3a of the measurement site holder 3 was manufactured as a negative impression of the finger of the individual patient, this measurement site holder 3 matches the finger shape of the individual patient. Accordingly, the finger 10 is positioned with a high degree of precision, and uniformly contacts the main body part 3a of the measurement site holder 3. In this case, furthermore, even if the nail grows, this nail protrudes from the nail opening part 33; accordingly, there is no interference with the high-precision positioning of the finger 10.

Next, when the measurement operation is performed, light from the light source 91 is caused to enter the interior of the main body part 3a of the measurement site holder 3 via the Michelson interferometer 92, focusing lens 93 and light-illumination opening part 31, so that a specified position on the finger 10 is illuminated. In this case, as was described above, the finger 10 is positioned with a high degree of precision, and uniformly contacts the main body part 3a of the measurement site holder 3; in addition, the measurement site holder 3 is positioned with a high degree of precision relative to the base 1. Accordingly, the incident light always illuminates substantially the same position on the finger 10, which shows no great variation in shape, so that the light that is transmitted through this finger 10 always passed through substantially the same position, and is then received by the photo-detector 5 via the light-detection opening part 32.

The photo-electrically converted signal from this photo-detector 5 is input into the computer system part 94, so that a near infrared spectrum is obtained. This near infrared spectral information and blood sugar levels obtained by blood collection performed at the same time as the measurement of the near infrared spectrum are input into the computer 60, and a working curve of the blood sugar levels is prepared on the basis of this information.

This working curve is recorded on the recording medium 11 of the measurement site holder 3 mounted on the current measuring device 50 (base 1). Since the measurement site holder 3 equipped with this recording medium 11 is detachable from the base 1 (on the side of the measuring device 50), the measurement site holder 3 can be carried or stored by the patient in question. Accordingly, a one-to-one correspondence is established between this measurement site holder 3 of the patient in question that is thus carried or stored, and the working curve for the patient in question.

Here, in measurements of blood sugar levels that are performed on subsequent occasions for the patient in question, the measurement site holder 3 for the exclusive use of the individual patient that is carried or stored by the patient in question (i.e., the same measurement site holder 3 as that described above) is mounted on the measuring device 50; then, the finger 10 of the patient in question is placed in the main body part 3a of the measurement site holder 3, so that a near infrared spectrum is obtained in the same manner as described above, and the computer 60 reads out the working curve that is recorded on the recording medium 11 of this measurement site holder 3 mounted on the measuring device 50.

Accordingly, this read-out working curve is the working curve for the patient in question. Furthermore, the computer 60 acquires blood sugar levels for the patient in question by comparing the near infrared spectrum that is obtained with the working curve for this patient.

The blood sugar levels thus acquired are recorded on the recording medium 11 of the measurement site holder 3 mounted on the measuring device 50. Accordingly, a one-to-one correspondence is also established between the blood sugar levels for this patient and the measurement site holder 3 for the exclusive use of the individual patient that is carried or stored.

Here, for example, in the case of diagnoses performed by physicians or evaluations performed by the patient himself, the computer 60 reads out the blood sugar levels recorded on the recording medium 11 of the measurement site holder 3 for the exclusive use of the individual patient that is carried or stored by the patient in question (i. e., the same measurement site holder 3 as that described above) from this same recording medium 11 (in this case, the measurement site holder 3 need not be mounted on the measuring device 50). Accordingly, these read-out blood sugar levels are the blood sugar levels of the patient in question, so that the above-mentioned diagnoses or evaluations are performed on the basis of these blood sugar levels for the patient in question.

Furthermore, in cases where the blood sugar levels of another patient are to be measured using this noninvasive optical bioinstrumentation device 50, the abovementioned measurement site holder 3 is removed, and a different measurement site holder 3 that was prepared for this other patient (and that matches the finger shape of this other patient) is mounted on the base 1, after which measurements are performed.

Furthermore, the working curves prepared by the computer 60 are prepared for each individual patient; accordingly, the working curve for the abovementioned other patient is recorded on the recording medium 11 of the different measurement site holder (measurement site holder of the other patient currently being measured) 3 that is mounted on the current measuring device 50, and the blood sugar levels that are acquired are also recorded on the recording medium 11 of this different measurement site holder 3 that is mounted on the current measuring device 50.

Thus, in the present embodiment, since a one-to-one correspondence is established between the measurement site holder 3 of a given patient and living-body information (working curve, blood sugar levels) for this patient, the erroneous acquisition of living-body information for individual patients can be prevented; e.g., erroneous diagnoses by physicians and erroneous evaluations by patients themselves can be prevented.

Furthermore, as a result of the use of this measurement site holder 3 equipped with a recording medium 11 for the patient in question, the acquisition of living-body information for the patient in question on subsequent occasions, and the read-out of living-body information for the patient in question, can be accomplished using a device other than the measuring device used to perform measurements. Accordingly, the convenience to the patient can be increased.

Furthermore, since the main body part 3a of the measurement site holder 3 for the exclusive use of the individual patient is manufactured in conformity to the shape of the finger 10 of the individual patient, so that the main body part and finger show substantial agreement in shape, the patient is more securely prevented from using the wrong measurement site holder 3. Accordingly, the erroneous acquisition of living-body information for individual patients is even more effectively prevented, so that erroneous diagnoses and erroneous evaluations are more securely prevented.

Furthermore, since such living-body information is recorded on the recording medium 11 of the measurement site holder 3 in a form that can be directly accessed by means of a personal computer or the like, this living-body information can be transmitted (for example) via a network 161 or the like that is connected to the computer 60 (160), so that the patient can be diagnosed by a physician in a remote location without any need for the patient to travel to the location of this physician; accordingly, the burden on the patient can be greatly reduced.

Furthermore, if such a network is utilized, then (for example) living-body information can be obtained by a remote operation from a remote location such as a hospital or the like in the case of use by elderly patients who are bedridden at home or the like.

Furthermore, in this embodiment, as was described above, the main body part 3a of the measurement site holder 3 is constructed using a negative impression of the finger for each individual patient; accordingly, the following effects and merits are obtained:

Specifically, since the main body part 3a of the abovementioned measurement site holder 3 matches the shape of the patient's finger 10, the finger 10 is positioned with a high degree of precision when the finger 10 is placed in the main body part 3a of the measurement site holder 3 at the time of light detection, so that shifting of the light path in the finger 10 is largely prevented. Accordingly, variation in the measured values caused by the non-uniform distribution of components in the living body is minimized; furthermore, the occurrence of minute variations in the shape of the finger 10 is largely prevented, so that variation in the measured values caused by variations in the light path length accompanying variations in the shape of the finger 10, and variations in blood flow or the like that accompany fine differences in the contact pressure, are minimized.

Accordingly, working curves can be prepared with a high degree of precision, and blood sugar levels can be quantitative measured with high precision, so that high-precision living-body information of these types can be recorded on the recording medium 11 of the measurement site holder 3 for the exclusive use of the individual patient.

The present inventors performed the following experiment in order to confirm that high-precision living-body information can be acquired by using the abovementioned measurement site holder 3 manufactured using negative impressions of the fingers of the individual patients.

In this experiment, a Spectrum 2000 FTIR manufactured by Perkin-Elmer Inc. was used as the Fourier transform near infrared spectroscopic analyzer 9, and an InGaAs-PIN photodiode (G5832-05 manufactured by Hamamatsu Photonics K.K.) was used as the photo-detector 5. The measurement wavelength range was set at 1.01 to 1.37 $\mu$m.

Then, after fasting for approximately 12 hours, each patient was caused to ingest a saccharine liquid (Trelan G75 manufactured by Shimizu Seiyaku K.K., glucose content 75 g). Blood was collected by pricking a finger tip on the left hand before ingestion of the saccharine liquid, and every 10 minutes up to 2 hours following the ingestion of the saccharine liquid. Immediately after blood collection, the blood serum was separated out by means of a centrifuge, and blood sugar levels were measured (analysis values according to a conventional method) using a clinical-chemical automatic analysis device (Spot-Chem manufactured by Kyoto Daiichi Kagaku K.K. (Arkray Inc.)). Meanwhile, measurements of the near infrared spectrum by means of the measurement site holder 3 were performed using the right hand at the time that blood was collected from the abovementioned finger tip of the left hand.

The preparation of working curves was accomplished using a partial least squares (PLS) regression analysis, with the blood sugar level obtained by means of the abovementioned blood collection used as the objective variable, and the near infrared spectrum measured at the same time as blood collection used as the descriptive variable. The predicted values of blood sugar levels according to the near infrared spectrum were calculated using the working curves thus prepared. The cross validation method was used in order to evaluate the precision of the working curves.

Figure 21:
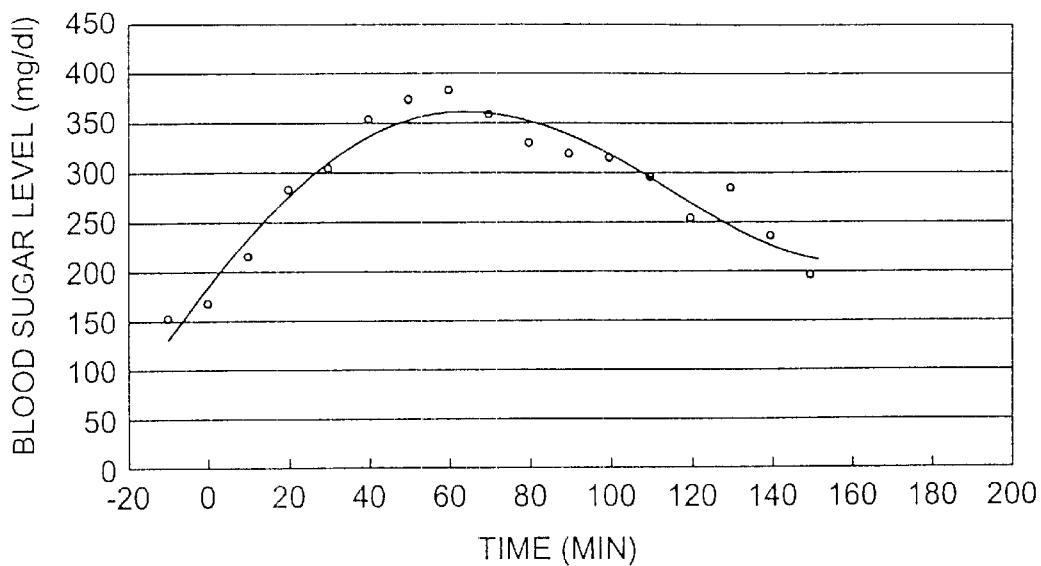
FIG. 21 is a graph which shows the variation over time of blood sugar levels obtained by blood collection following ingestion of a saccharine liquid.
Figure 22:
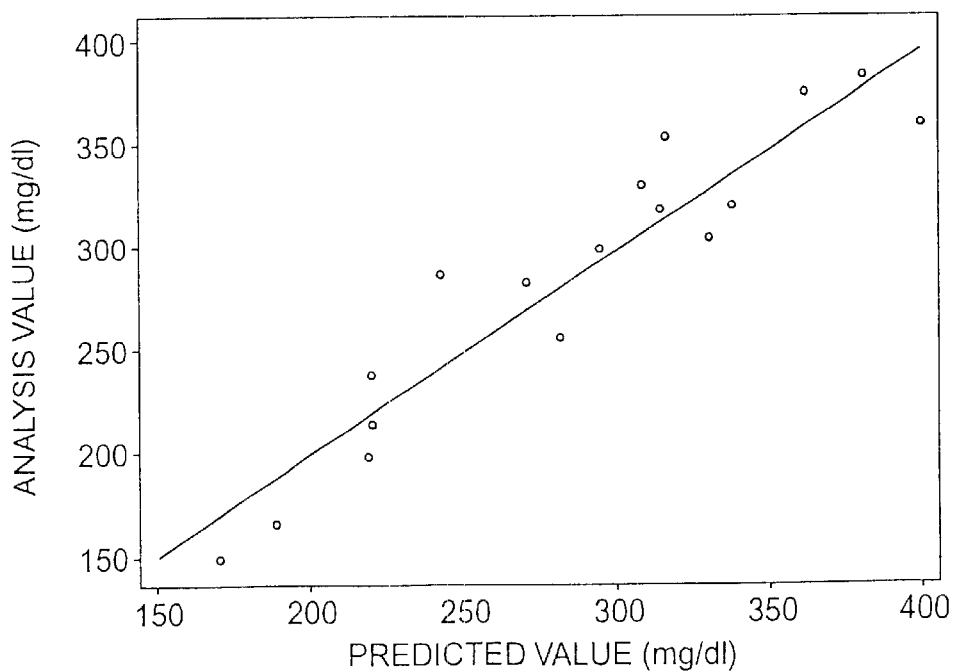
FIG. 22 is a graph which shows the correlation between analysis values obtained by blood collection and predicted values according to the near infrared spectrum.

FIG. 21 is a graph which shows change over time in the blood sugar levels (analysis values) obtained by blood collection following the ingestion of the abovementioned saccharine liquid. FIG. 22 is a graph which shows the correlation between analysis values obtained by blood collection and predicted values according to the near infrared spectrum. As is shown in FIG. 21, the analysis values for the patients obtained by blood collection fluctuated over a range of 150 to 383 mg/dl.

Meanwhile, as a result of PLS regression analysis using the cross validation method, the correlation coefficient between the analysis values obtained by blood collection and the predicted values according to the near infrared spectrum was 0.94 (see FIG. 22) with the number of factors (number of variables with minimal RMSEP) estimated at 7, and the root means square error of prediction (RMSEP) was 23 mg/dl.

Specifically, it was confirmed that blood sugar levels can be quantitatively measured with a high degree of precision by using the abovementioned measurement site holder 3 manufactured using negative impressions of the fingers of individual patients.

Figure 23A:
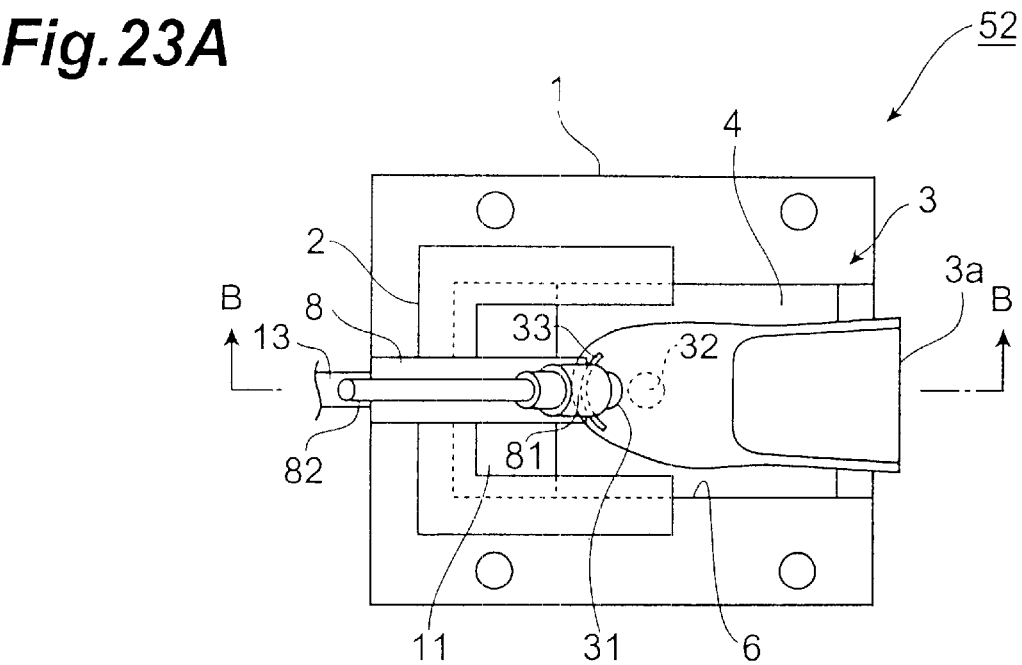
FIG. 23A is a plan view of another measurement site holding device mounting the measurement site holder of the noninvasive optical bioinstrumentation device of the fifteenth embodiment.
Figure 23B:
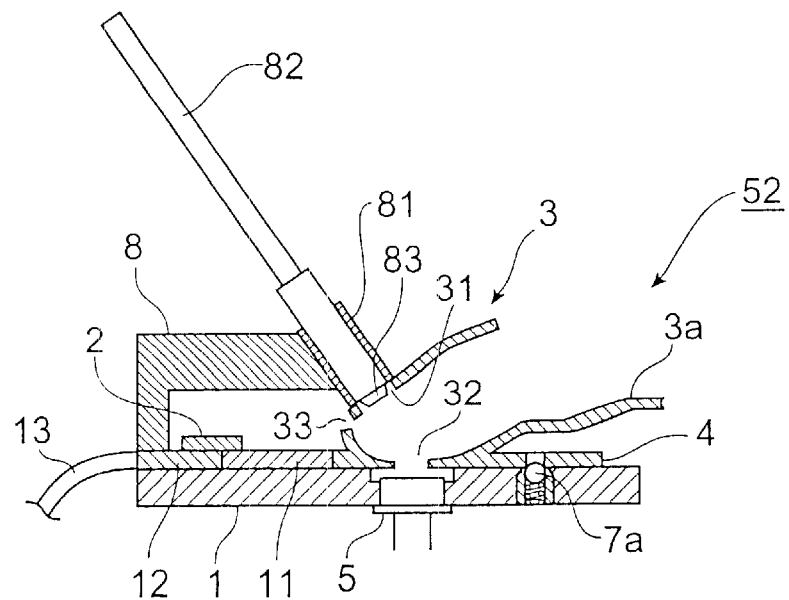
FIG. 23B is a sectional view along line XXIII—XXIII of the device shown in FIG. 23A.

FIG. 23A is a plan view of another measurement site holding device mounting the measurement site holder of the fifteenth embodiment, and FIG. 23B is a sectional view along line XXIII—XXIII in FIG. 23A.

The measurement site holding device 52 shown in these FIGS. 23A and 23B differs from the measurement site holding device 51 shown in FIGS. 19, 20A and 20B in that this device is constructed so that illuminating light is guided by an optical fiber 82 and caused to illuminate the finger 10 in the same manner as in the device shown in FIGS. 5A and 5B.

Specifically, the measurement site holding device 52 is further equipped with an optical fiber supporting base 8 which is disposed on the end portion of the base 1 located on the opposite side from the side where the base plate 4 is inserted, and which has a shape that extends from this end portion and covers the light-illumination opening part 31 of the measurement site holder 3 from above. Furthermore, the measurement site holding device 52 is also equipped with a guide 81 which is located on this optical fiber supporting base 8 in a position corresponding to the light-illumination opening part 31 of the abovementioned measurement site holder 3, and which has an inclined shape that is coaxial with the abovementioned light-illumination opening part 31. The tip end portion of the optical fiber 82 that is used to illuminate the finger 10 is inserted into this guide 81 so that the optical fiber 82 can slide.

Furthermore, as is shown in FIG. 23, a computer is connected to the recording medium 11 installed in the measurement site holder 3 via a recording medium connecting connector 12 and recording medium connecting cable 13.

In the measurement site holding device 52 constructed as described above, the emitting end 83 of the optical fiber 82 can always be accurately positioned inside the light-illumination opening part 31 by sliding the optical fiber 82, even if a measurement site holder 3 with a main body part 3a which has a different size (because of the size of the patient's finger) is mounted on the base 1 and the finger 10 is placed in this measurement site holder 3.

Accordingly, in addition to the abovementioned effects, the variation in the measured values can be further minimized regardless of the size of the patient's finger, so that blood sugar levels can be quantitatively measured with a much higher degree of precision.

Furthermore, it would also be possible to install an optical fiber that guides the light transmitted through the finger 10 into the photo-detection system in the installation position of the photo-detector 5. Furthermore, in cases where optical fibers are thus used in both positions, it would also be possible to use the opening part 31 and the optical fiber located on the side of this opening part 31 for light detection, and to use the opening part 32 and the optical fiber located on the side of this opening part 32 for light illumination.

Sixteenth Embodiment

Figure 24:
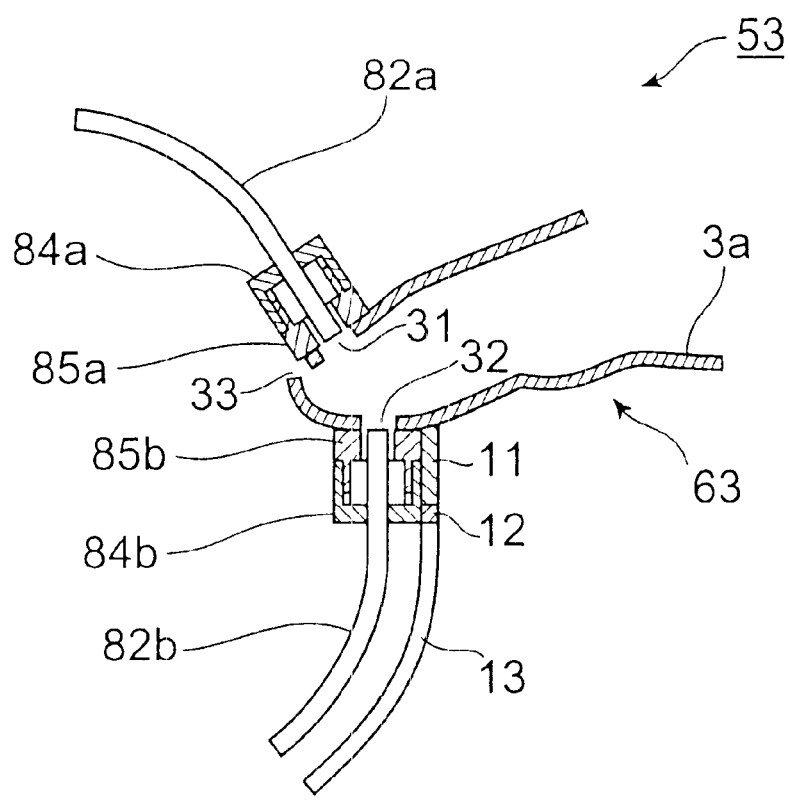
FIG. 24 is a sectional view of a measurement site holding device mounting the measurement site holder of a noninvasive optical bioinstrumentation device constituting a sixteenth embodiment of the present invention.

FIG. 24 is a sectional view the measurement site holder mounted in the measurement site holding device of a noninvasive optical bioinstrumentation device constituting a sixteenth embodiment of the present invention.

This sixteenth embodiment differs from the fifteenth embodiment in that the measurement site holder is a measurement site holder 63 which is equipped with a main body part 3*a* (of a construction similar to that described above) in which the finger 10 is placed, an optical fiber receiving fitting 85*a* which has a tubular shape and which surrounds the light-illumination opening part 31 of the main body part 3*a* on the outer surface of the main body part 3*a*, an optical fiber receiving fitting 85*b* which has a tubular shape and which surrounds the light-detection opening part 32 of the main body part 3*a* on the outer surface of the main body part 3*a*, and a recording medium 11 which is fastened to this optical fiber receiving fitting 85*b* (as in the embodiment shown in FIG. 6), and in that the measurement site holding device is a measurement site holding device 53 which is equipped with the abovementioned measurement site holder 63, an optical fiber retaining fitting 84*a* on the side of the measuring device 50, which mounts an optical fiber 82*a* that is used to illuminate the finger 10, and which is detachably mounted on the optical fiber receiving fitting 85*a*, and an optical fiber retaining fitting 84*b* on the side of the measuring device 50, which mounts an optical fiber 82*b* that is used to guide that light that is transmitted through the finger 10 into the photo-detection system, and which is detachably mounted on the optical fiber receiving fitting 85*b*.

Various constructions may be used as concrete constructions that allow these optical fiber retaining fittings 84*a* and 84*b* to be respectively attached to or detached from the optical fiber receiving fittings 85*a* and 85*b*; for example, screws that are screw-engaged with each other or grooves and protruding parts that engage with each other may be used.

Furthermore, the device is constructed so that the light-illumination opening part 31, optical fiber receiving fitting 85*a*, optical fiber retaining fitting 84*a* and optical fiber 82*a* are coaxially positioned, and so that the light-detection opening part 32, optical fiber receiving fitting 85*b*, optical fiber retaining fitting 84*b* and optical fiber 82*b* are coaxially positioned. Furthermore, the optical fiber receiving fittings 85*a* and 85*b*, and the optical fiber retaining fittings 84*a* and 84*b*, are constructed so that these respective fittings have the same shape.

It goes without saying that the same effects as those obtained in the fifteenth embodiment can also be obtained in this construction; in addition, since the transmission and reception of light to and from the finger 10 are performed using optical fibers 82*a* and 82*b*, measurements can be performed on patients in locations that are separated from the main body side of the noninvasive optical bioinstrumentation device 50.

Furthermore, the recording medium 11 may also be mounted on the optical fiber receiving fitting 85*a*, or may be mounted directly on the main body part 3*a*. In short, it is sufficient if the recording medium 11 is mounted on a measurement site holder 63 that is detachable from the measuring device 50, so that the recording medium 11 can be carried or stored by the patient in question.

Furthermore, a construction may also be used in which a photo-detector which has a housing that is detachable from the measurement site holder 63 is mounted on the light-detection opening part 32 of this measurement site holder 63, so that light can be detected by this photo-detector via the light-detection opening part 32.

Furthermore, a construction may also be used in which a light-emitting element which has a housing that is detachable from the measurement site holder 63 is mounted on the light-illumination opening part 31 of this measurement site holder 63, so that light illumination can be performed by this light-emitting element via the light-illumination opening part 31.

Furthermore, as was described in FIGS. 23A and 23B, the opening part 31 and the optical fiber 82*a* on the side of this opening part 31 can also be used for light detection, and the opening part 32 and the optical fiber 82*b* on the side of this opening part 32 can also be used for light illumination.

Seventeenth Embodiment

As the next embodiment, a case in which light quantity levels used for measurement (constituting measurement parameter information) are stored on the recording medium disposed in the measurement site holder 3 in addition to living-body information for the individual patient will be described with reference to FIG. 25.

Figures 25A, 25B:
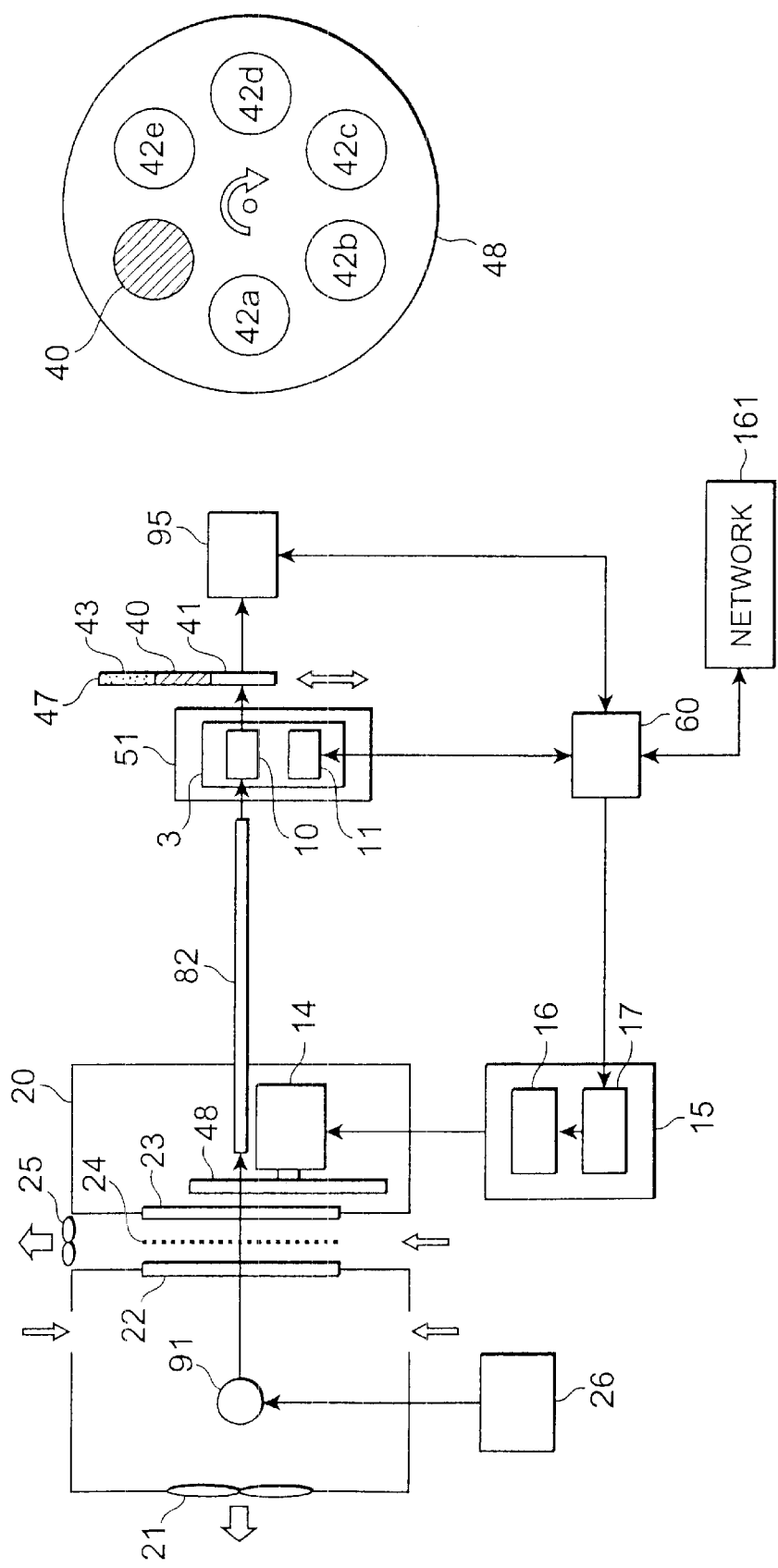
FIG. 25A is a structural diagram of a noninvasive optical bioinstrumentation device constituting a seventeenth embodiment of the present invention.
FIG. 25B is a front view of the circular turret 48 used as the light adjustment means in the noninvasive optical bioinstrumentation device.

FIG. 25A is a structural diagram of a noninvasive optical bioinstrumentation device constituting a seventeenth embodiment of the present invention, and FIG. 25B is a front view of a circular turret 48 used as light adjustment means in this noninvasive optical bioinstrumentation device.

The computer 60 reads out light quantity level information for the individual patient from the recording medium 11 installed on the measurement site holder 3, and inputs rotational amount information for a servo motor 14 into a motor control part 15. Then, on the basis of this information, the control circuit 17 of the motor control part 15 inputs a pulse signal that indicates the amount by which the servo motor 14 is to be driven into a motor driver 16. The motor driver 16 drives the servo motor 14 in accordance with the input pulse signal, and thus controls the rotational angle of the circular turret 48.

In the circular turret 48, as is shown in FIG. 25B, a light-blocking plate 40 and a plurality of light-reducing plates 42*a*, 42*b*, 42*c*, 42*d* and 42*e* with different light reduction rates are disposed on the circumference of the same circle, and the circular turret 48 can be rotated by any desired amount by means of a servo motor 14 whose rotating shaft is attached to the center of the circle in a perpendicular attitude. Thus, the quantity of light can be adjusted to a light quantity that matches the measurement light quantity level for the individual patient stored on the recording medium 11 by rotating the circular turret 48 so that an appropriate light-reducing plate 42 is selected.

The reason for setting the measurement light quantity according to individual patients is as follows: specifically, there are individual differences in the quantity of transmitted light or diffused and reflected light from the measurement site, caused by differences in the thickness of the measurement site of the patient in the case of transmitted light, and by differences in the spacing between the light-illuminated part and the part that receives the diffused and reflected light, differences in skin color, differences in the surface conditions of the skin and the like in the case of diffused and reflected light. Accordingly, in order to perform high-precision measurements, it is necessary to adjust the light quantity level of the light that illuminates the measurement site so that this is a light quantity at which the photo-detector has an optimal S/N ratio. Furthermore, the light that passes through the circular turret 48 is conducted to the light-illumination opening part 31 (see FIG. 26) via an optical fiber 82.

The sliding type turret 47 is disposed on the light-detection opening part 32 side of the measurement site holding device 51 (see FIG. 27), and is equipped with a light-blocking plate 40, an aperture 41 and a reference plate 43, which are separated from each other. The sliding type turret 47 reduces or narrows down the light on the light path by positioning the respective plates in the light path of the transmitted light from the measurement position 10.

Prior to the initiation of the measurement process, in order to stabilize the light source 91, the lamp power supply 26 is switched on, and at the same time, a cooling fan 25 is operated. 1.5 minutes after the light source 91 has been lit, a cooling fan 21 disposed in the lamp housing 20 is operated. After a further 3.5 minutes has elapsed, the quantity of the light emitted from the light source 91 is stabilized. Following this stabilization of the light quantity, measurement of the reference spectrum (described below) and measurement of the transmitted light from the measurement site 10 are performed.

In the present example, an incandescent light source with a power of 50 W to 100 W is used as the light source 91. Furthermore, since a high-stability light source 91 has a large power consumption, the quantity of light is large, and the quantity of heat that is generated is also large; accordingly, there may be cases in which the light source is too bright, or cases in which the heat causes changes or deterioration in the quality filters or optical fibers over time. In the device of the present embodiment, in order to allow adjustment of the light quantity with the light from a stable light source kept "as is" in a stable state, and in order to inhibit any deterioration, the abovementioned circular turret 48 is employed, and the heat absorbing filter 22 and visible light cutting filter 23 are cooled by a fan 25. To describe this in detail, a ventilation path is formed by the cooling fan 25 for the heat absorbing filter 22 and visible light cutting filter 23, which are installed facing each other.

In this case, at the same time that the lamp power supply 26 that supplies electric power to the lamp 91 is switched on, the heat absorbing filter 22, visible light cutting filter 23 and metal mesh 24 are cooled by the cooling fan 25, which is attached to the side surface of the lamp housing 20.

First, the circular turret 48 located on the light path of the lamp housing 20 is rotated so that the light is blocked; at the same time, the sliding type turret 47 is caused to slide so that the light-blocking plate 40 is inserted into the light path, and the background noise of the spectrometer 95 is measured.

Next, the sliding type turret 47 which is located on the light path between the measurement site holding device 51 and the spectrometer 95 is caused to slide so that the reference plate 43 is inserted into the light path; at the same time, the circular turret 48 located on the light path of the lamp housing 20 is rotated so that the light-reducing plate 42 that produces the predetermined light quantity level is inserted into the light path. Then, the reference spectrum is measured by the spectrometer 92. The measured data is stored in the computer 60.

Afterward, the sliding type turret 47 is caused to slide so that the reference plate 43 is removed from the light path, after which the light-blocking plate 40 is inserted into the light path; at the same time, the circular turret 48 is rotated so that the light-blocking plate 40 is inserted into the light path extending from the light source 91 to the sliding type turret 47.

Next, the measurement site holder 3 constructed using a negative impression of the measurement site 10 of the individual patient is inserted into the measurement site holding device 51, and the measurement site 10 of the patient is placed in this measurement site holder 3. In this case, the patient's name, the measurement light quantity level for the individual patient and information concerning the working curve, which are recorded on the recording medium 11 attached to the measurement site holder 3, are transferred to the computer 60.

When the measurement site 10 is thus placed in the measurement site holder 3, a contact sensor 3y (see FIG. 27) disposed inside the measurement site holder 3 senses the placement of the measurement site 10, so that the placement of the measurement site 10 is confirmed. At the same time, the circular turret 48 is caused to rotate on the basis of the measurement light quantity level for the patient that has been transferred to the computer 60, so that the light-reducing plate (one of the plates 42a through 42e) that corresponds to the measurement light quantity level for the individual patient is inserted into the light path. Furthermore, the sliding type turret 47 is caused to slide so that the light-blocking plate 40 is removed from the light path, and the aperture 41 is inserted into the light path. Then, the transmitted light from the measurement site 10 on the light path of the lamp is splited into its spectrum components by the spectrometer 95, so that a near infrared spectrum is obtained.

When the measurement process is completed, the circular turret 48 is caused to rotate so that the light is blocked, and the sliding type turret 47 is caused to slide so that the light-blocking plate 40 is inserted into the light path. The blood sugar level is then predicted by the computer 60 on the basis of this near infrared spectrum and the working curve.

When the abovementioned measurements are performed, it is necessary to select the quantity of light that is emitted from the light source 91 for the individual patient. In this case, for example, if the light quantity is adjusted by varying the voltage that is supplied to the light source 91, the color temperature of the light source (incandescent light bulb such as a halogen lamp, tungsten lamp or the like) will vary so that the spectroscopic characteristics vary; as a result, the spectrum that is obtained will vary.

If feedback control of the light source 91 is accomplished by means of voltage control, the mechanism becomes mechanically complicated; furthermore, if the voltage is varied, time is required for stabilization. In the present embodiment, instead of light quantity control based on the voltage, the quantity of light is adjusted by means of the optical system (aperture or slit, diaphragm, ND filter, or liquid crystal element) 22, 23, 48, 47, so that the color temperature that accompanies a change in the quantity of light is fixed, thus fixing the spectral distribution that is obtained.

If an appropriate light quantity is determined, reproducibility can be increased by performing subsequent measurements using this light quantity. Furthermore, since the apertures that are used (42a through 42e) are determined for each individual patient, this aperture information is stored on the recording medium 11 as a measurement parameter. In this construction, the measurement site 10 can be illuminated with highly stable light; accordingly, reproducible measurement results can be obtained.

This device has a function which makes it possible to adjust the light quantity without varying the color temperature, so that adjustments can be performed by means of the optical system 48 on the basis of information from a recording medium 11 that stores the light quantity used for individual patients, in a noninvasive optical bioinstrumentation device in which a specified measurement site 10 in the living body is illuminated with light, the light that is transmitted through this measurement site 10 or the light that is diffused and reflected by this measurement site 10 is detected, and the concentrations of components in the living body are measured from this detected light. Furthermore, the recording medium 11 is mounted on the measurement site holder 3; however, this recording medium 11 may also be accommodated in the computer 60.

In the abovementioned device, there is no need to search for the optimal light quantity for each measurement, so that the efficiency of the device is increased; furthermore, the device is very simple, and therefore highly reliable in mechanical terms. Measurements for more than one patient can be performed by rotating the circular turret 48.

In the abovementioned embodiment, the measurement light quantity level is cited as an example of a measurement parameter. However, measurement parameters are not limited to this; the exposure time and number of times of integration of the spectrometer detector, the spacing between the light-illuminated part and the diffused and reflected light receiving part, the control temperature of the measurement site and the like may also be cited as examples of measurement parameters.

The rotary type circular turret 48 may also be a sliding type mechanism, a removable mechanism or a liquid crystal element.

Depending on the power consumption of the light source 91 that is used, it may not be necessary to cool the heat absorbing filter 22, visible light cutting filter 23 or metal mesh 24 with a cooling fan 25.

The spectrometer 95 may be a dispersion type spectrometer, a Fourier transform type spectrometer or an interference filter type spectrometer.

The reference plate 43 may be a scattering plate, aperture, diaphragm, slit or ND filter.

Furthermore, the measurement site holder 3 will be described again.

Figure 26:
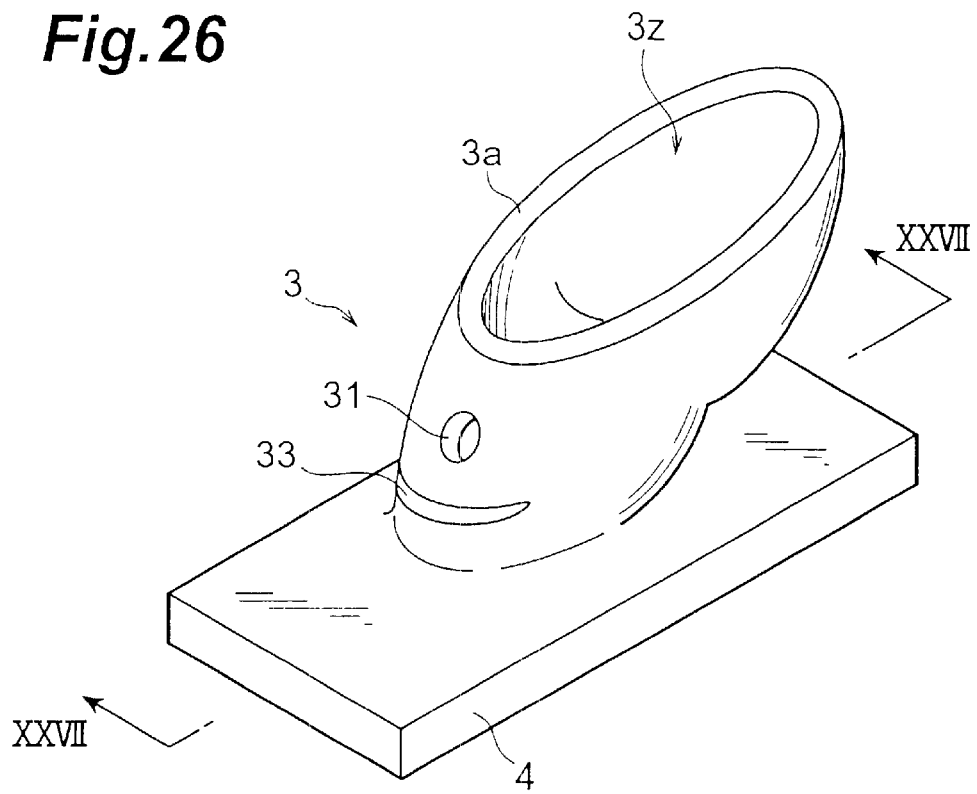
FIG. 26 is a perspective view of the measurement site holder 3.
Figure 27:
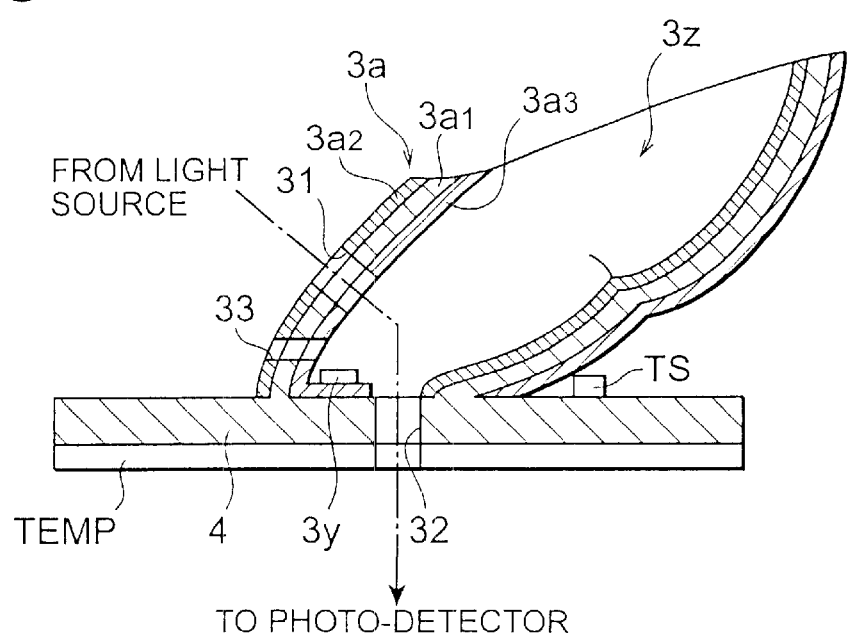
FIG. 27 is a sectional view along line XXVII—XXVII of the measurement site holder 3 shown in FIG. 26.

FIG. 26 is a perspective view which shows the abovementioned measurement site holder 3 in detail, and FIG. 27 is a sectional view along line XXVII—XXVII of the measurement site holder 3 shown in FIG. 26.

The measurement site holder 3 is a measurement site holder which is attached to a base 1 (see FIG. 1) disposed in the light path of the light that is incident on the abovementioned photo-detection system. This measurement site holder 3 is equipped with a main body part 3a which has an opening (insertion opening) 3z into which the measurement site 10 (see FIG. 1) is inserted, and a base plate 4 to which at least the tip end of the main body part 3a is fastened, and which can be detached from the base 1. The main body part 3a has a crescent-moon-shaped opening part 33. When the finger is inserted into the insertion opening 3z as the measurement site 10, the nail of this finger protrudes from the opening part 33.

The main body part 3a that has the measurement site insertion opening 3z consists of a molded resin 3a_1. The outside surface of this molded resin (except for the opening parts 31 and 33) is covered by a metal thin film (aluminum) 3a_2, and the inside surface is coated or covered with a black coating material 3a_3. The metal thin film 3a_2 blocks stray light from the outside, and the black coating material 3a_3 causes attenuation of the light that is reflected by the inside surface.

The measurement site holder 3 is equipped with a sensor 3y which outputs a signal that indicates when the measurement site 10 has been placed in the measurement site holder 3. This sensor 3y is a contact sensor in which a mechanical switch is switched ON by the application of pressure, a piezoelectric sensor which converts pressure into an electrical signal, or an electrostatic capacitance sensor which senses variations in electrostatic energy. This sensor 3y is attached to the inside of the main body part 3a. When the measurement site 10 presses against the sensor 3y, the sensor 3y outputs a signal indicating that this has occurred, and the abovementioned measurement process is initiated on the basis of this signal.

The measurement site holder 3 is equipped with a temperature regulating element TEMP that regulates the temperature of the measurement site holder 3; this element TEMP is a cooling element that cools the measurement site holder 3 or a heating element that heats the measurement site holder 3. In this example, the temperature regulating element TEMP is attached to the bottom face of the base plate 4. Furthermore, the measurement site holder 3 has a temperature sensor TS on the upper surface of the base plate 4; this sensor indirectly detects the temperature of the measurement site 10. Furthermore, the attachment positions of these parts may be altered.

Next, the method used to manufacture the abovementioned measurement site holder 3 will be described.

First, the measurement site is coated with an unhardened resin (impression material), or the measurement site is inserted into such an unhardened resin. Then, the resin is hardened so that a first resin mold (female mold) which has an inside surface that matches the shape of the outside surface of the measurement site is formed (negative impression). Next, an unhardened resin is introduced into the interior of this first resin mold, and this resin is then hardened so that a second resin mold (male mold) which has an outside surface of the same shape as the measurement site is formed. Furthermore, the outside surface of the second resin mold is coated with an unhardened resin, or the second resin mold is inserted into an unhardened resin, and this resin is then hardened so that a main body part 3a which has an inside surface that matches the shape of the outside surface of the measurement site is formed.

Afterward, the tip end portion of the main body part 3a is fastened to the surface of the base plate 4. Next, opening parts 31, 32 and 33 are formed, and a metal thin film 3a_2 is formed on the outside surface of the main body part 3a (consisting of this molded resin 3a_1) by a plating process or vacuum evaporation process, and the inside surface of the main body part 3a is coated with a black coating material 3a_3. Afterward, the measurement site holder is completed by attaching the various elements and sensors mentioned above in specified positions.

In the case of such a manufacturing method, the time required to manufacture the first resin mold (female mold) is short; accordingly, the time for which the patient must be restrained in order to manufacture this mold can be shortened. Furthermore, the first resin mold and second resin mold can be manufactured at (for example) a hospital or examination center; then, these molds can be transported to a specified factory, and the manufacturing process of the measurement site holder can be performed at this specified factory. Furthermore, if the second resin mold is available, the main body part 3a and base plate 4 can also be molded as an integral unit. In the case of such integrated molding, the manufacture of the measurement site as a direct mold is difficult; accordingly, if such integrated molding is performed at a specified factory, a high-precision measurement site holder 3 can be provided. Such a high-precision measurement site holder 3 makes it possible to perform even higher-precision measurements.

Specifically, the abovementioned manufacturing method comprises the steps of forming a first resin mold which has an inside surface that matches the shape of the outside surface of the measurement site, forming a second resin mold which has an outside surface of the same shape as the outside surface of the abovementioned measurement site by introducing a resin into the first resin mold, transporting the abovementioned second resin mold to a specified factory, and forming a measurement site holder which has an inside surface that matches the shape of the outside surface of the abovementioned second resin mold at the abovementioned factory.

Figure 28:
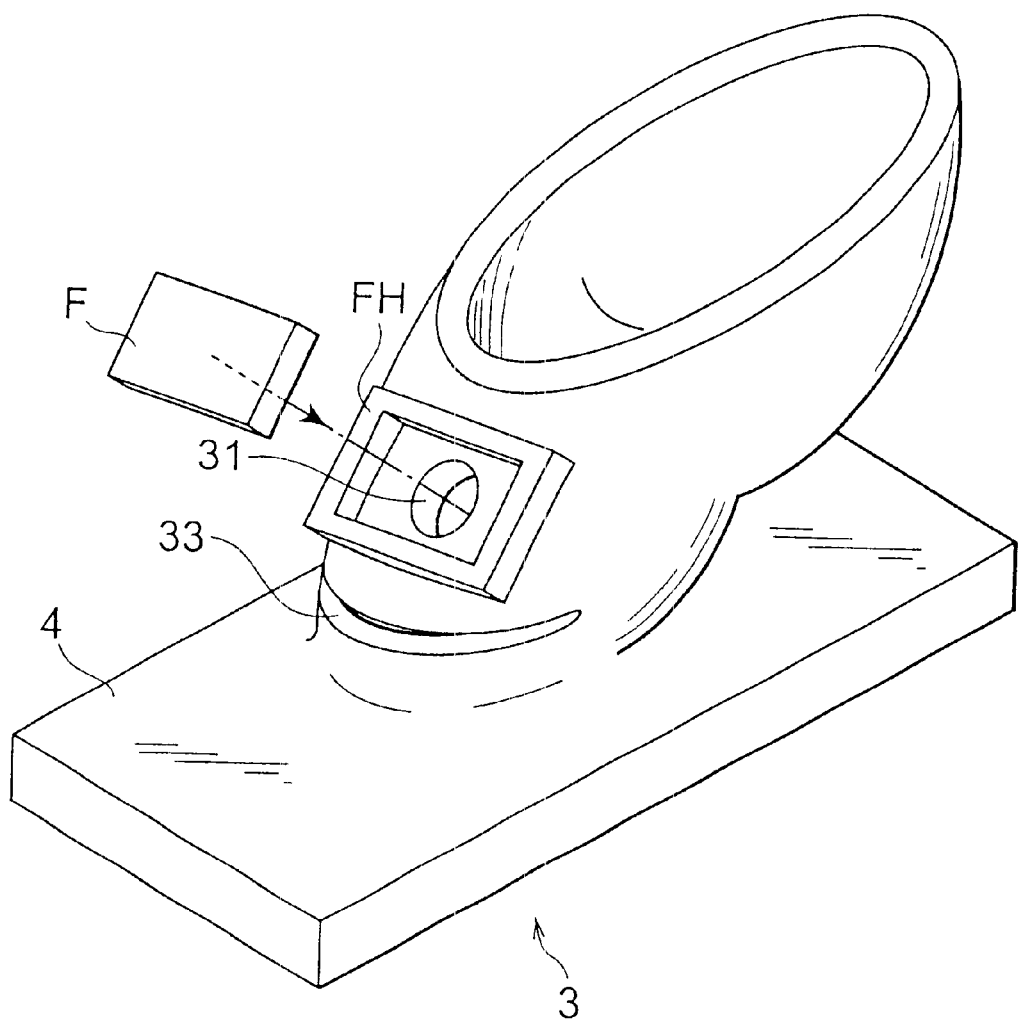
FIG. 28 is a partial perspective view of the measurement site holder 3.

FIG. 28 is a partial perspective view of the measurement site holder 3. A filter holder FH is formed as an integral part of the main body part 3*a* around the opening part 31, and an (optical) filter F is fastened inside this filter holder FH. Specifically, the measurement site holder 3 is equipped with an optical filter F that is attached to the outside surface of the main body part 3*a*. The optical filter F has characteristics that are matched to the individual patient. This optical filter functions as a light-blocking plate in the same manner as the abovementioned turret; accordingly, the information for this optical filter F is naturally recorded on the abovementioned recording medium 11. In this case, the abovementioned turret 48 is unnecessary; however, such a turret may be used as required.

Furthermore, the present invention is not limited to the abovementioned embodiments. For example, in the abovementioned embodiments, the living-body information for the individual patients consists of near infrared spectra, working curves, and blood sugar levels determined using these near infrared spectra and working curves, and of these data, the working curves and blood sugar levels are recorded on the recording medium 11. However, it would also of course be possible to record the near infrared spectra as well.

Furthermore, it would also be possible to use a construction in which the computer 60 is installed on the side of the measurement site holder 3 or 63 separately from the measuring device 50 (i.e., forming a measurement site holder 3 or 63 that is equipped with a computer 60 and recording medium 11), and in which this computer 60 is connected to the measuring device 50 as required.

Furthermore, in the abovementioned embodiments, the main body part 3*a* of the measurement site holder 3 or 63 is manufactured as a negative impression of the finger of each individual patient (in order to achieve a sufficient function); however, it would also be possible (for example) to prepare measurement site holders 3 or 63 that have main body parts 3*a* of numerous different sizes, and to select and use a measurement site holder 3 or 63 that fits the finger of the patient.

In this case, the measurement precision drops compared to a case where the main body part 3*a* of the measurement site holder 3 or 63 is manufactured as a negative impression of he finger of each individual patient as in the abovementioned embodiments; however, since the main body part 3*a* of the measurement site holder 3 fits the patient's finger, the finger 10 is positioned with good precision when the finger 10 is placed in the main body part 3*a* of the measurement site holder 3 or 63 at the time of light detection, so that the shift of the light path in the finger 10 is small compared to that seen in conventional devices. Accordingly, variation in the measured values caused by the non-uniform distribution of components in the living body can be reduced, and variations in the shape of the finger 10 are reduced compared to conventional devices, so that variations in the measured values caused by variations in the light path length that accompany variations in the shape of the finger, and by variations in blood flow or the like that accompany differences in the contact pressure, can be reduced. As a result, the concentrations of components in the living body can be quantitatively measured with good precision.

Furthermore, in the embodiments in which transmitted light from the measurement site is detected, it would also be possible to use a construction in which light that is diffused and reflected from the measurement site is detected, and in embodiments in which light that is diffused and reflected from the measurement site is detected, it would also be possible to use a construction in which transmitted light from the measurement site is detected. In the case of diffused and reflected light, as was described above, an opening that makes it possible to guide reflected light that is diffused and reflected from the measurement site into the photo-detection system is formed in the same surface (upper side) as the light-illumination opening part of the measurement site holder 3. Of course, as was described in the abovementioned embodiments, it is also possible to install (for example) a photo-detector or an optical fiber used for light detection in a position corresponding to this opening part.

Furthermore, in cases where reflected light that is diffused and reflected from the measurement site is thus detected, it is also possible to use a common part for the light-illumination opening part and light-detection opening part. In concrete terms (for example, in the sixteenth embodiment), an optical fiber bundle is used.

Furthermore, the use of a measurement site holder 3 or 63 equipped with a recording medium 11 is not limited to a measuring device which measures living-body information spectroscopically. For example, such a measurement site holder may also be used in measuring device that measures living-body information magnetically or by other means.

Furthermore, in the abovementioned embodiments, the finger 10 is used as an especially desirable measurement site; however, other sites such as the feet, legs, hands, arms, forehead, ear lobes or the like may also of course be used.

Furthermore, in the abovementioned embodiments, the material of the measurement site holder 3 is an ordinary-temperature polymerizing resin; however, this material may also of course be an impression material or thermoplastic resin.

Furthermore, in the measurement of the reference spectrum and interferograms based on transmitted light from the living body in the fourth embodiment, two types of data, i.e., data obtained with the polarization directions of the polarizer 72 and analyzer 74 of the birefringent interferometer 70 set parallel to each other, and data obtained with these polarization directions set perpendicular to each other, are acquired in order to improve the S/N ratio; however, it would also be possible to acquire only one or the other of these types of data. In such a case, measurements can be performed in a short time, so that such a method is effective in cases where the concentrations of components in the living body fluctuate at a rapid rate.

Furthermore, in the fourth through twelfth embodiments and the fourteenth embodiment, the noninvasive optical bioinstrumentation device is equipped with a sliding type turret 47; however, it would also be possible to use a circular turret 147 in these embodiments. Furthermore, the aperture plate 41, light-reducing plate 42 and light-reducing plates 42a through 42d with different light reduction rates that are disposed on these turrets may be manufactured using any parts such as apertures, diffusing plates, ND filters, slits, meshes and the like.

Furthermore, in the abovementioned embodiments, glucose is cited as an example of a component in the living body. However, the present invention is not limited to this; for example, blood proteins, red blood cell concentrations (hematocrit value), albumin, globulin, cholesterol, neutral fats, phospholipids, lipoproteins, lipid peroxide, urea, uric acid, alcohol, aldehyde, lactic acid, glycohemoglobin and the like may also be cited as examples of such components.

In the abovementioned measurement site holder 3, when the measurement site of the patient in question is set in a measurement site holder exclusively for the use of the individual patient that is mounted on the side of the measuring device, living-body information acquired for the patient in question and measurement parameters for this patient are recorded on the recording medium of the measurement site holder that is currently mounted on the measuring device. Meanwhile, since this measurement site holder is made detachable from the measuring device, the measurement site holder can be carried or stored by the patient in question, so that a one-to-one correspondence is established between this measurement site holder for the patient in question that is carried or stored and used for measurements, and living-body information for this patient. Accordingly, the device is constructed so that the erroneous acquisition of living-body information and measurement parameters for individual patients can be prevented; furthermore, the device is constructed so that the acquisition of living-body information for the patient in question on subsequent occasions, and the read-out of recorded living-body information for the patient in question, can be accomplished using a device other than the measuring device used to perform measurements, by using this measurement site holder for the patient in question that is equipped with a recording medium. Consequently, erroneous diagnoses and erroneous evaluations can be prevented, and the convenience to the patient can be improved.

Furthermore, since the abovementioned noninvasive optical bioinstrumentation device is equipped with a measurement site holder that is constructed using a negative impression of the measurement site, this measurement site holder can be caused to match or fit the shape of the measurement site of the patient, so that the measurement site is positioned with good precision when the measurement site is placed in the measurement site holder at the time of light detection, thus reducing the shift of the light path in the measurement site compared to that seen in conventional devices, so that variation in the measured values caused by the non-uniform distribution of components in the living body is reduced, and so that variations in the shape of the measurement site are reduced compared to the variations seen in conventional devices. Accordingly, variation in the measured values caused by variations in the light path length accompanying variations in the shape of the measurement site, and by variations in blood flow or the like accompanying differences in the contact pressure can be reduced. Consequently, the concentrations of components in the living body can be quantitatively measured with good precision.

Industrial Applicability

The present invention can be utilized in living body measuring devices and measurement site holders.

What is claimed is:

1. A noninvasive optical bioinstrumentation device in which a specified measurement site in the living body is illuminated with light, the light that is transmitted through this measurement site or the light that is scattered and reflected by this measurement site is detected by a photo-detection system, and the concentrations of components in the living body are measured from this detected light, wherein the device is equipped with a measurement site holder which is constructed using a negative impression of the measurement site, and in which the measurement site is placed at the time of light detection.

2. The noninvasive optical bioinstrumentation device according to claim 1, wherein said measurement site holder has a structure which is detachable from a base that is disposed in the light path of the light that is incident on said photo-detection system.

3. The noninvasive optical bioinstrumentation device according to claim 2, wherein said measurement site holder is equipped with a recording medium which records living-body information acquired from the individual patient and/or measurement parameters used at the time of measurement.

4. The noninvasive optical bioinstrumentation device according to claim 3, wherein the living-body information for the individual patient that is recorded on said recording medium is a working curve for said individual patient and information concerning components in the living body of said individual patient that is determined using this working curve.

5. The noninvasive optical bioinstrumentation device according to claim 3, wherein the living-body information for said patient is determined on the basis of said detected light.

6. The noninvasive optical bioinstrumentation device according to claim 5, wherein said measurement site holder is manufactured so as to match the shape of said measurement site of said individual patient.

7. The noninvasive optical bioinstrumentation device according to claim 1, wherein said measurement site holder is manufactured as a negative impression of the measurement site of each individual patient.

8. The noninvasive optical bioinstrumentation device according to claim 1, wherein said measurement site holder is equipped with an opening part that allows the illumination of said measurement site with light, and an opening part that makes it possible to guide the transmitted light or diffused and reflected light from said measurement site into said photo-detection system.

9. The noninvasive optical bioinstrumentation device according to claim 1, wherein said measurement site holder is equipped with an opening part which makes it possible to illuminate said measurement site with light, and which also makes it possible to guide diffused and reflected light from said measurement site to said photo-detection system.

10. The noninvasive optical bioinstrumentation device according to claim 1, wherein the inside contact surface of said measurement site holder that contacts said measurement site is coated with a coating material that absorbs light in the measurement wavelength region.

11. The noninvasive optical bioinstrumentation device according to claim 1, wherein said photo-detection system is equipped with a birefringent interferometer which converts said transmitted light or said diffused and reflected light into split light by using a polarized light splitting birefringent element to split said light into polarized light with mutually perpendicular vibrational planes, and which causes said split light to converge so that an interferogram that makes it possible to measure the concentrations of said components in the living body is obtained.

12. The noninvasive optical bioinstrumentation device according to claim 11, wherein said birefringent interferometer comprises:
- a polarizer which polarizes said transmitted light or said diffused and reflected light and directs this light onto said polarized light splitting birefringent element;
- an analyzer which polarizes said split light emitted from said polarized light splitting birefringent element;
- converging means which cause convergence of the light polarized by said analyzer and thus form said interferogram; and
- a photo-detector which detects this interferogram.

13. The noninvasive optical bioinstrumentation device according to claim 11, wherein light adjustment means that narrow down or reduce said transmitted light or said diffused and reflected light are disposed between said measurement site holder and said birefringent interferometer.

14. The noninvasive optical bioinstrumentation device according to claim 11, wherein said polarized light splitting birefringent element is a Savart plate.

15. The noninvasive optical bioinstrumentation device according to claim 11, wherein said polarized light splitting birefringent element is a Wollaston prism.

16. The noninvasive optical bioinstrumentation device according to claim 1, wherein said measurement site holder is equipped with a sensor which outputs a signal that indicates when said measurement site has been placed in this measurement site holder.

17. The noninvasive optical bioinstrumentation device according to claim 16, wherein said sensor is a contact sensor in which a mechanical switch is switched ON by the application of pressure.

18. The noninvasive optical bioinstrumentation device according to claim 16, wherein said sensor is a piezoelectric sensor.

19. The noninvasive optical bioinstrumentation device according to claim 1, wherein said measurement site holder is equipped with a cooling element that cools this measurement site holder.

20. The noninvasive optical bioinstrumentation device according to claim 1, wherein said measurement site holder is equipped with a heating element that heats this measurement site holder.

21. The noninvasive optical bioinstrumentation device according to claim 1, wherein said measurement site holder is equipped with a temperature sensor.

22. The noninvasive optical bioinstrumentation device according to claim 1, wherein said measurement site holder is equipped with a main body part that is made of a resin containing a pigment or dye that absorbs light in the measurement wavelength region, and that contacts said measurement site.

23. A measurement site holder which is attached to a base that is disposed in the light path of light that is incident on a photo-detection system, said measurement site holder being characterized by comprising a main body part which has an opening into which the measurement site is inserted, and a base plate to which at least the tip end of said main body part is fastened, and which is detachable from said base, wherein the main body part has a crescent-moon-shaped opening part.

24. The measurement site holder according to claim 23, wherein a metal thin film is formed on the outside surface of said measurement site holder, and the inside surface of said measurement site holder is coated with a black coating material.

25. The measurement site holder according to claim 23, wherein said holder is equipped with an optical filter that is attached to the outside surface of said main body part.

\* \* \* \* \*